(12) United States Patent
Chappell et al.

(10) Patent No.: US 8,067,433 B2
(45) Date of Patent: Nov. 29, 2011

(54) METHODS, COMPOSITIONS, AND KITS FOR THE TREATMENT OF OPHTHALMIC DISORDERS

(75) Inventors: Todd W. Chappell, Boston, MA (US);
M. James Nichols, Boston, MA (US);
Daniel S. Grau, Arlington, MA (US)

(73) Assignee: Zalicus Inc., Cambridge, MA (US)

( * ) Notice: Subject to any disclaimer, the term of this patent is extended or adjusted under 35 U.S.C. 154(b) by 916 days.

(21) Appl. No.: 11/594,428

(22) Filed: Nov. 8, 2006

(65) Prior Publication Data

US 2007/0105761 A1    May 10, 2007

Related U.S. Application Data

(60) Provisional application No. 60/735,989, filed on Nov. 9, 2005.

(51) Int. Cl.
*A61K 38/13* (2006.01)
*A61K 31/573* (2006.01)
(52) U.S. Cl. ............................ 514/300; 514/58; 514/179
(58) Field of Classification Search .............. 514/9, 11, 514/58, 179, 912; 424/482, 486, 488
See application file for complete search history.

(56) References Cited

U.S. PATENT DOCUMENTS

| | | | |
|---|---|---|---|
| 4,512,978 A | 4/1985 | Inwood | |
| 4,569,935 A | 2/1986 | Rosenberg et al. | |
| 4,839,342 A | 6/1989 | Kaswan | |
| 5,411,952 A * | 5/1995 | Kaswan | 514/11 |
| 5,474,979 A | 12/1995 | Ding et al. | |
| 5,981,607 A | 11/1999 | Ding et al. | |
| 6,254,860 B1 | 7/2001 | Garst | |
| 6,331,313 B1 | 12/2001 | Wong et al. | |
| 6,369,116 B1 * | 4/2002 | Wong et al. | 514/171 |
| 6,677,304 B2 * | 1/2004 | Di Napoli | 514/9 |
| 6,809,077 B2 | 10/2004 | Or et al. | |
| 6,872,705 B2 | 3/2005 | Lyons | |
| 2003/0216431 A1 | 11/2003 | Raut | |
| 2004/0151754 A1 | 8/2004 | Ashton | |
| 2004/0152664 A1 * | 8/2004 | Chang et al. | 514/58 |
| 2004/0180868 A1 | 9/2004 | Mullally | |
| 2004/0259863 A1 | 12/2004 | Eggenweiler et al. | |
| 2005/0059583 A1 | 3/2005 | Acheampong et al. | |
| 2005/0112069 A1 | 5/2005 | Beume et al. | |
| 2005/0112199 A1 | 5/2005 | Padval et al. | |
| 2005/0192261 A1 | 9/2005 | Jost-Price et al. | |
| 2005/0256081 A1 | 11/2005 | Peyman | |
| 2005/0277584 A1 | 12/2005 | Tien et al. | |
| 2006/0002963 A1 | 1/2006 | Rabinovich-Guilatt et al. | |
| 2006/0003982 A1 | 1/2006 | Williams et al. | |
| 2006/0122152 A1 | 6/2006 | Peyman | |
| 2006/0148686 A1 * | 7/2006 | Xia et al. | 514/11 |
| 2007/0225217 A1 | 9/2007 | Chappell et al. | |

FOREIGN PATENT DOCUMENTS

| | | |
|---|---|---|
| JP | 05310591 A | 11/1993 |
| WO | WO 03/000289 A1 | 1/2003 |
| WO | WO 2006/050965 A1 | 5/2004 |
| WO | WO 2004/069267 | 8/2004 |
| WO | WO 2004/096216 | 11/2004 |
| WO | WO 2005/027839 A2 | 3/2005 |

OTHER PUBLICATIONS

Birnbaum et al., "Immunosuppression with cyclosporine A and mycophenolate mofetil after penetrating high-risk keratoplasty: a retrospective study" Transplantation Apr. 27, 2005;79(8):964-968.
Lim et al., "Serpiginous choroiditis" Surv Ophthalmol. May-Jun. 2005;50(3):231-244.
Menezo et al., "Clinical outcome of chronic immunosuppression in patients with non-infectious uveitis" Clin Exper Ophthalmol Feb. 2005;33(1):16-21.
Nguyen et al., "Tyndallometry in monitoring therapy of sympathetic ophthalmia" Klin Monatsbl Augenheilkd. Jan. 1994;204(1):33-36.
Sajjadi et al., "Low dose cyclosporine-A therapy in Behcet's Disease" J Ocul Pharmacol. 1994 Fall;10(3):553-560.
Sra et al., "New trends in ocular allergy" Clin Surg Ophthalmol. Apr. 2005;23(4):136-142.
Utech et al., "Treatment of Graves Ophthalmopathy with Cyclosporin A Alone and in Combination with Corticosteroids" Acta Endocrinol Suppl (Copenh). 1985 08(267):72.
Zierhut et al., "Immunosuppressive therapy with mycophenolate mofetil (CellCept) in treatment of uveitis" Ophthalmologe. Jul. 2001;98(7):647-651.
Extended European Search Report for European Application No. EP 10 00 1901; Dated Jul. 1, 2010.
Mizoguci et al., "Cyclosporin Ointment for Psoriasis and Atopic Dermatitis," *The Lancet* 339(8801): 1120, 1992.
Al-Torbak et al., "Deep Corneal Neovascularization After Implantation With Intrastromal Corneal Ring Segments" Am J Ophthalmol Nov. 2005;140(5):926-927.
Anderson and Regillo "Ocular manifestations of graft versus host disease" Curr Opin Ophthalmol. Dec. 2004;15(6):503-507.
Chung et al., "Confocal Microscope Findings in a Case of Delayed-onset Bilateral Diffuse Lamellar Keratitis after Laser In Situ Keratomileusis," J. Cataract Refract. Surg. 28:1467-1470, 2002.
Hakin et al., "Sympathetic Ophthalmia: Visual Results with Modern Immunosuppressive Therapy," Eye:453-455,1992.
Kosrirukvongs et al., "Vernal Keratoconjunctivitis in Thailand" Asian Pac J Allergy Immunol Mar. 2003;21(1):25-30.
Mills et al., "Effect of Immunosuppression on Outcome Measures in a Model of Rat Limbal Transplantation" Invest Ophthalmol Vis Sci. Mar. 2002;43(3):647-655.
Muhaya et al., "Behçet's Disease in Japan and in Great Britain: a Comparative Study" Ocul Immunol Inflamm Sep. 2000;8(3):141-148.
Nussenblatt et al., "Randomized, Double-Masked Study of Cyclosporine Compared to Prednisolone in the Treatment of Endogenous Uveitis" Am. J. Opthalmol. 112:138-146, 1991.

(Continued)

*Primary Examiner* — Michael G Hartley
*Assistant Examiner* — Jagadishwar Samala
(74) *Attorney, Agent, or Firm* — Clark & Elbing LLP

(57) ABSTRACT

The invention features methods, kits, and compositions for the treatment of ophthalmic disorders. The compositions include a corticosteroid in combination with a non-steroidal immunophilin-dependent immunosuppressant.

6 Claims, 19 Drawing Sheets

OTHER PUBLICATIONS

Ogawa et al., "Successful Treatment of Dry Eye in Two Patients With Chronic Graft-Versus-Host Disease With Systemic Administration of FK506 and Corticosteroids" Cornea May 2001:20(4):430-434.

Perry et al., "Topical Cyclosporine A 0.5% as a Possible New Treatment for Superior Limbic Keratoconjunctivitis" Ophthalmology. Aug. 2003;110(8):1578-1581.

Rao, "Treatment of Herpes Simplex Virus Stromal Keratitis Unresponsive to Topical Prednisolone 1% With Topical Cyclosporine 0.05%" Am J Ophthalmol. Apr. 2006;141(4):771-772.

Wehrly et al., "Cytomegalovirus Keratitis After Penetrating Keratoplasty" Cornea. Nov. 1995;14(6):628-633.

Whitcup et al., "Topical Cyclosporine Inhibits Mast Cell-Mediated Conjunctivitis," Invest. Opthalmol. Vis. Sci. 37:2686-2693, 1996.

Williams et al., "A Comparison of the Effects of Topical Cyclosporine and Topical Steroid on Rabbit Corneal Allograft Rejection" Transplantation. Mar. 1985;39(3):242-244.

Zhang et al., "The Effect of Corticosteroid and Cyclosporin A on Murine Corneal Allograft Rejection" Graefes Arch Clin Exp Ophthalmol. Jun. 2000;238(6):525-530.

International Search Report for PCT/US2006/043493, Dated: Jul. 12, 2007.

Office Action (U.S. Appl. No. 11/594,436), mailed Mar. 30, 2010.

Supplemental European Search Report for PCT/US2006/043493, Dated: Nov. 27, 2009.

* cited by examiner

Fig. 1A. Dexamethasone x Cyclosporine Anti-Inflammatory TNF Alpha P/I PBMC
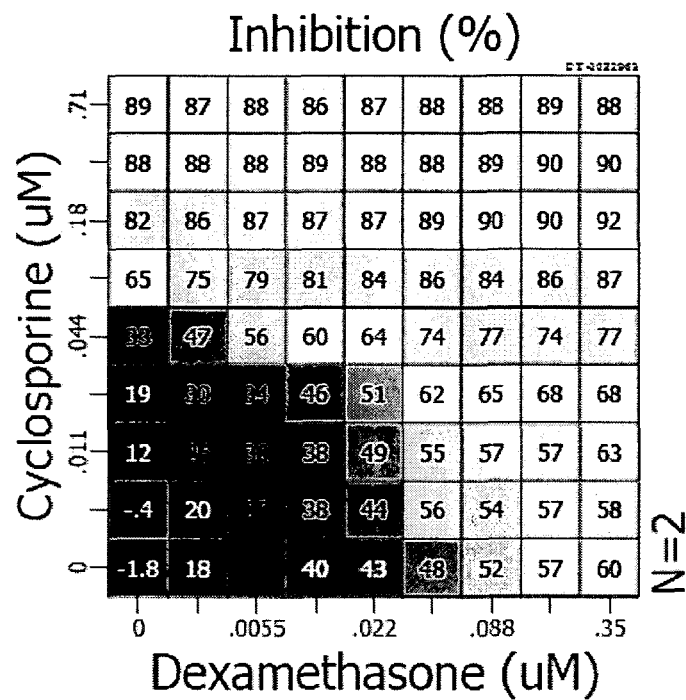
Fig. 1B. Dexamethasone x Cyclosporine Anti-Inflammatory IFN Gamma P/I PBMC
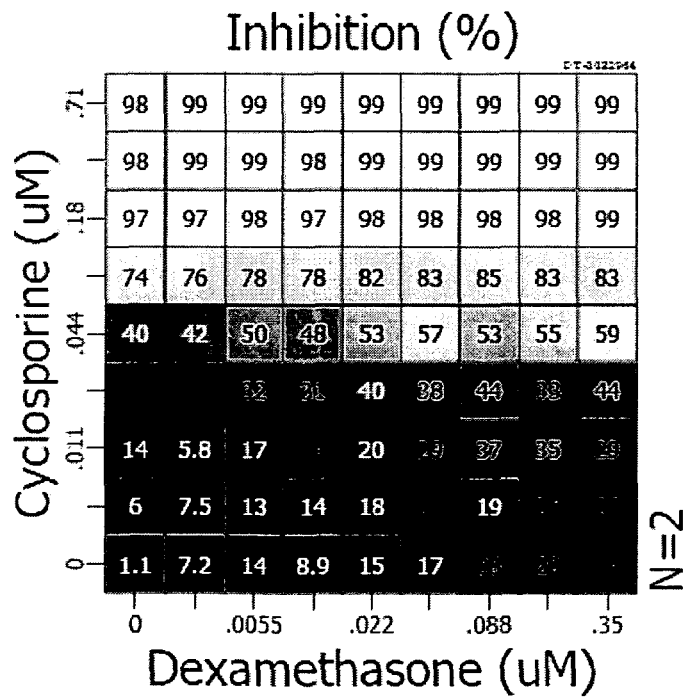

Fig. 1C. Dexamethasone x Cyclosporine Anti-Inflammatory IL2 P/I PBMC
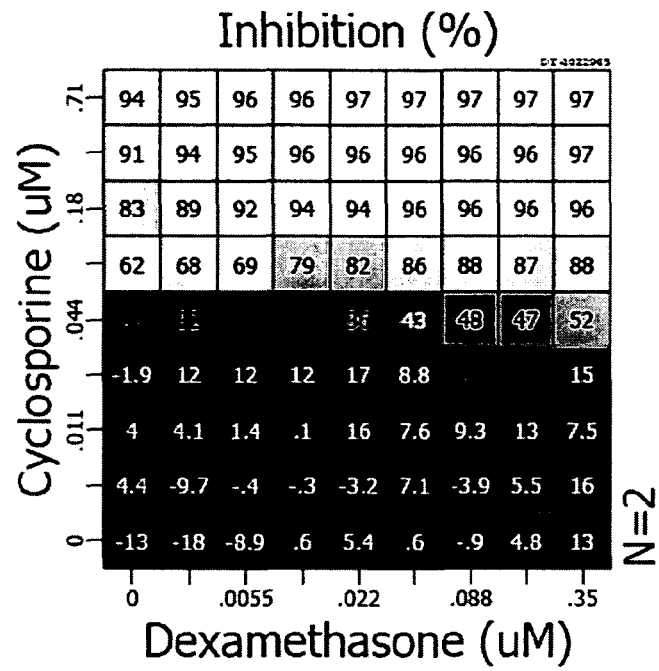
Fig. 1D. Fluorometholone x Cyclosporine Anti-Inflammatory TNF Alpha P/I PBMC
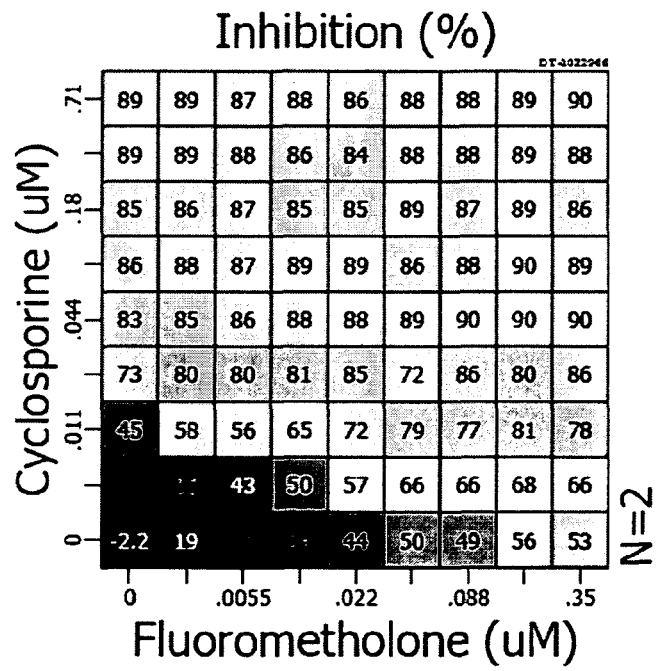

Fig. 1E. Fluorometholone x Cyclosporine Anti-Inflammatory IFN Gamma P/I PBMC
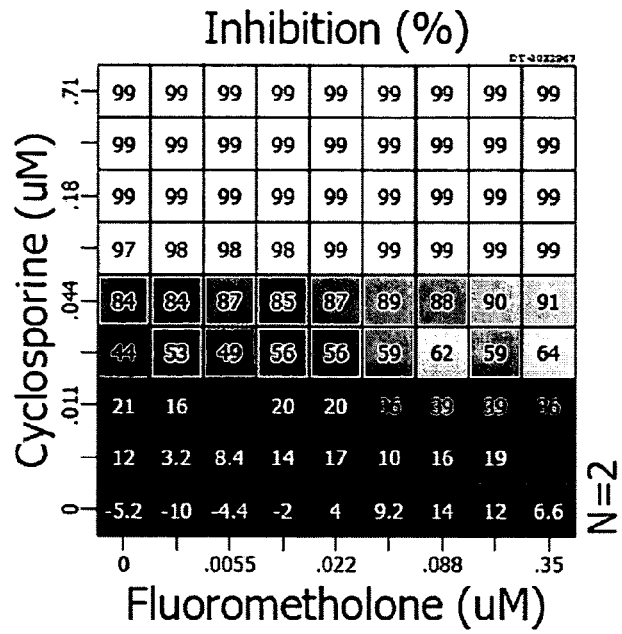
Fig. 1F. Fluorometholone x Cyclosporine Anti-Inflammatory IL2 P/I PBMC
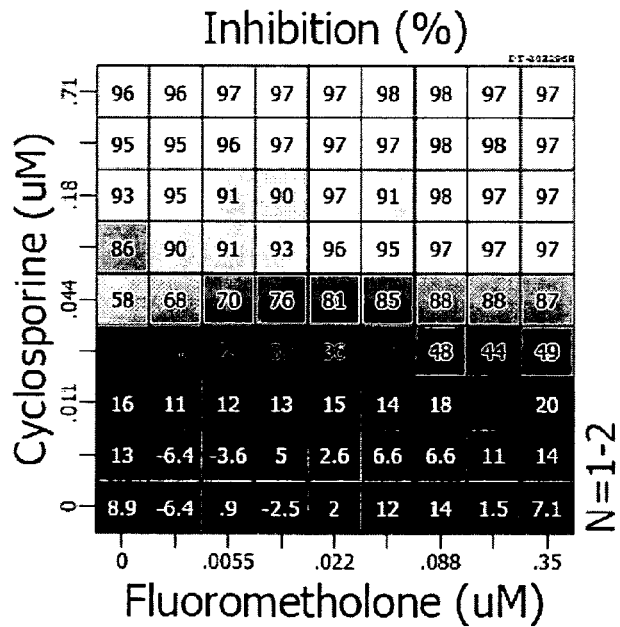

Fig. 1G. Hydrocortisone x Cyclosporine Anti-Inflammatory TNF Alpha P/I PBMC
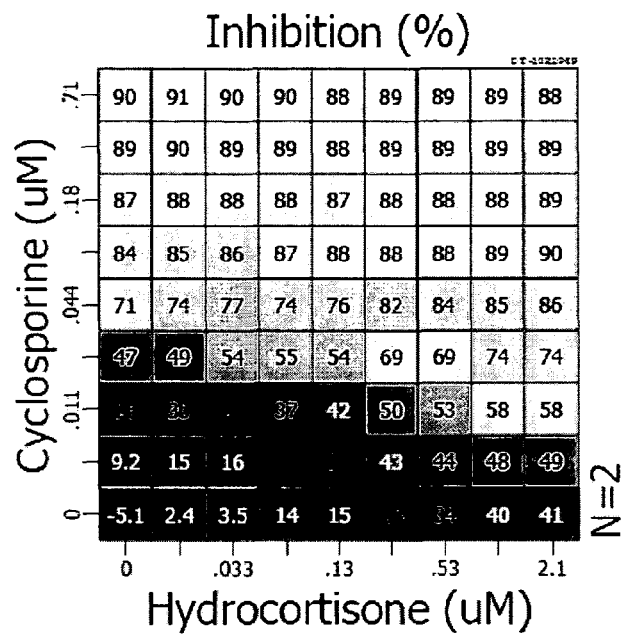
Fig. 1H. Hydrocortisone x Cyclosporine Anti-Inflammatory IFN Gamma P/I PBMC
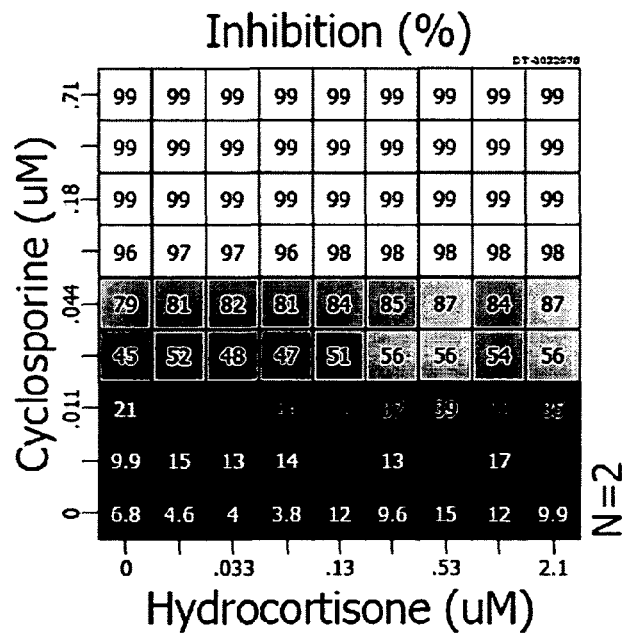

Fig. 1I. Hydrocortisone x Cyclosporine Anti-Inflammatory IL2 P/I PBMC
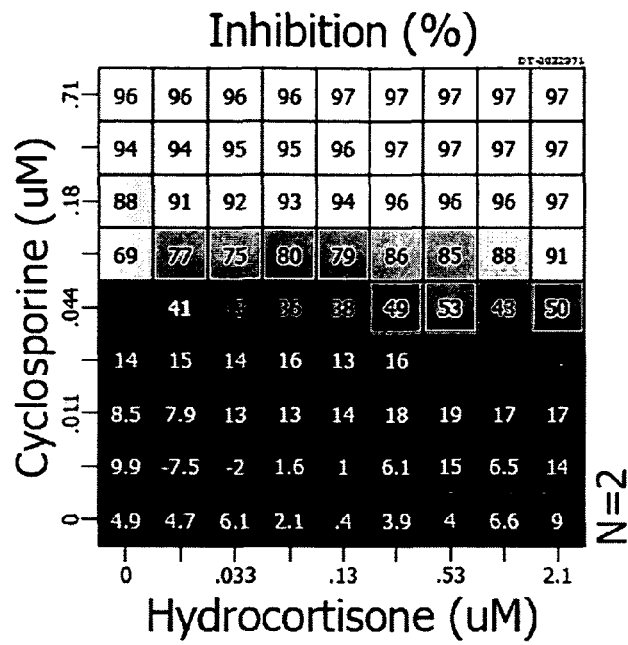
Fig. 1J. Loteprednol Etabonate x Cyclosporine Anti-Inflammatory TNF Alpha P/I PBMC
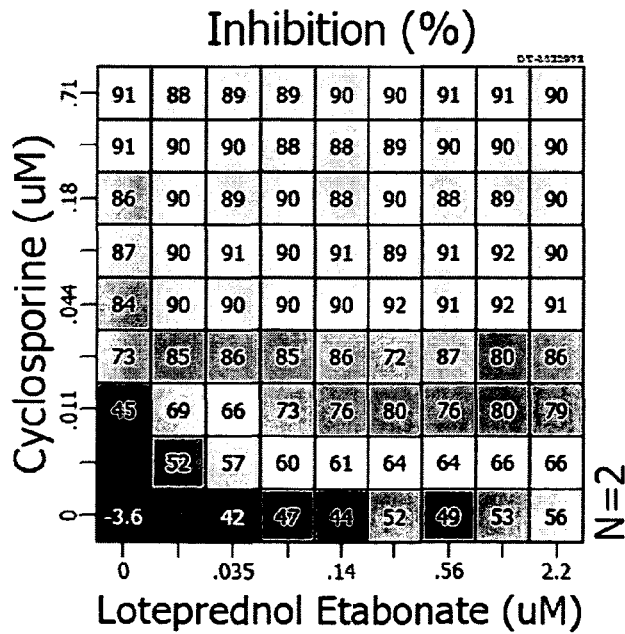

Fig. 1K. Loteprednol Etabonate x Cyclosporine Anti-Inflammatory IFN Gamma P/I PBMC
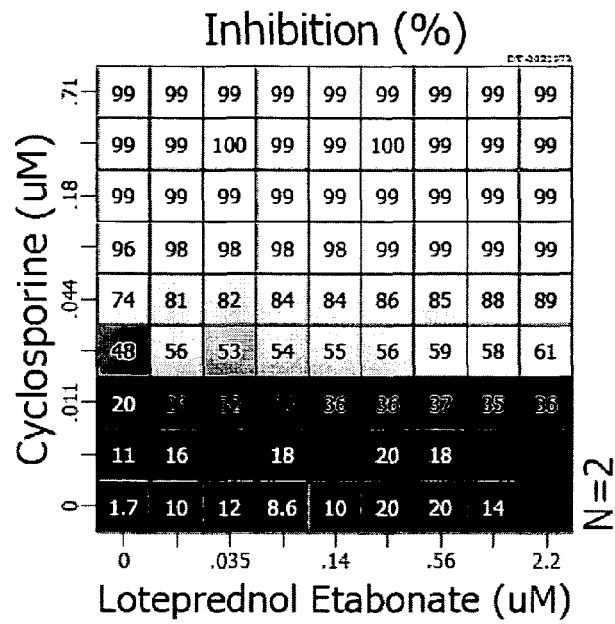
Fig. 1L. Loteprednol Etabonate x Cyclosporine Anti-Inflammatory IL2 P/I PBMC
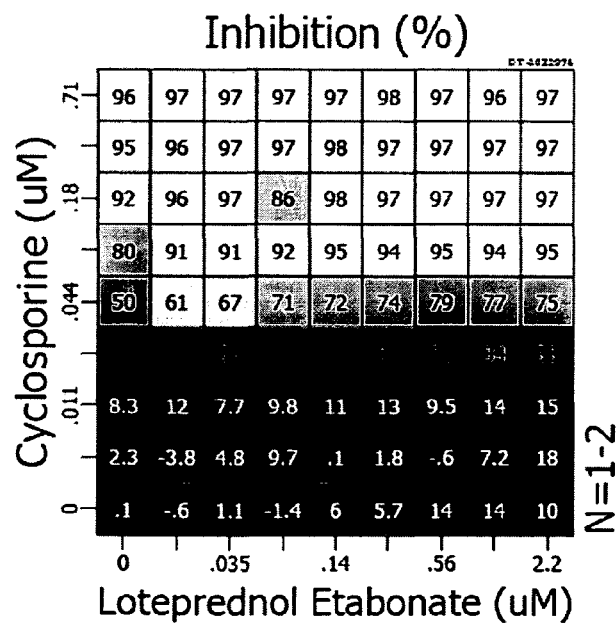

Fig. 1M. Medrysone x Cyclosporine Anti-Inflammatory TNF Alpha P/I PBMC
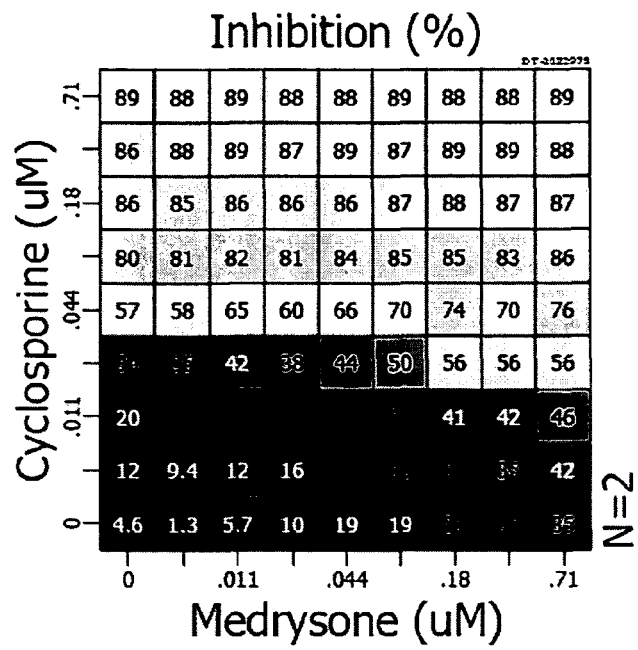
Fig. 1N. Medrysone x Cyclosporine Anti-Inflammatory IFN Gamma P/I PBMC
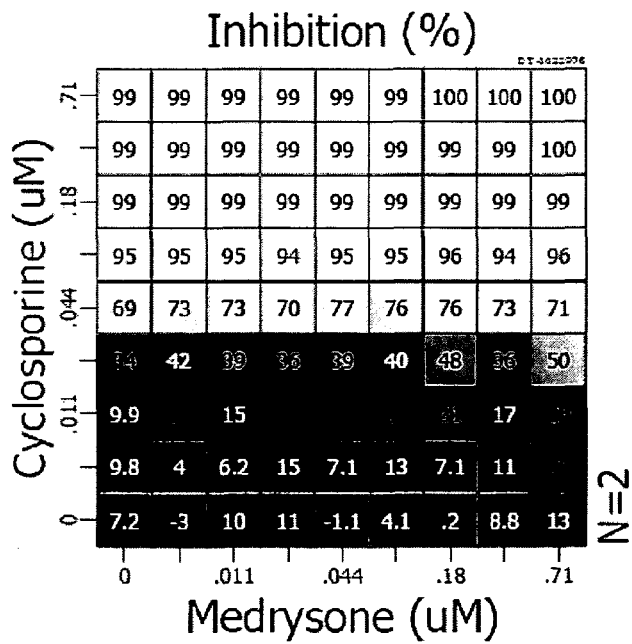

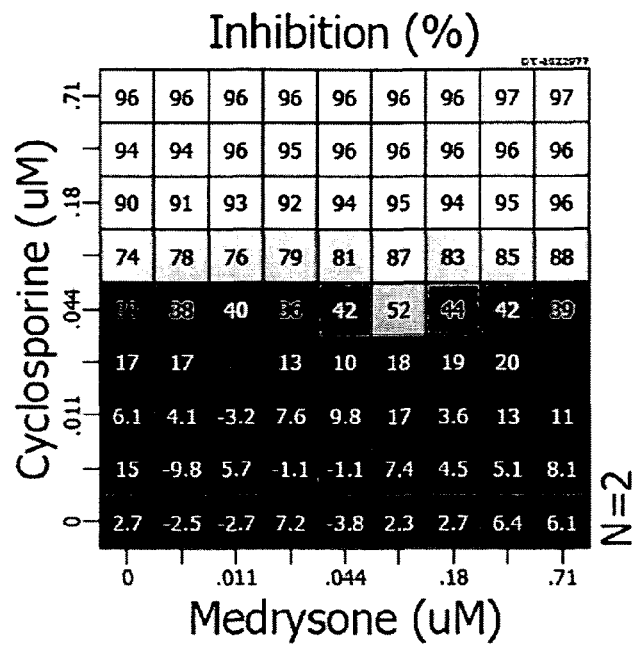
Fig. 1O. Medrysone x Cyclosporine Anti-Inflammatory IL2 P/I PBMC
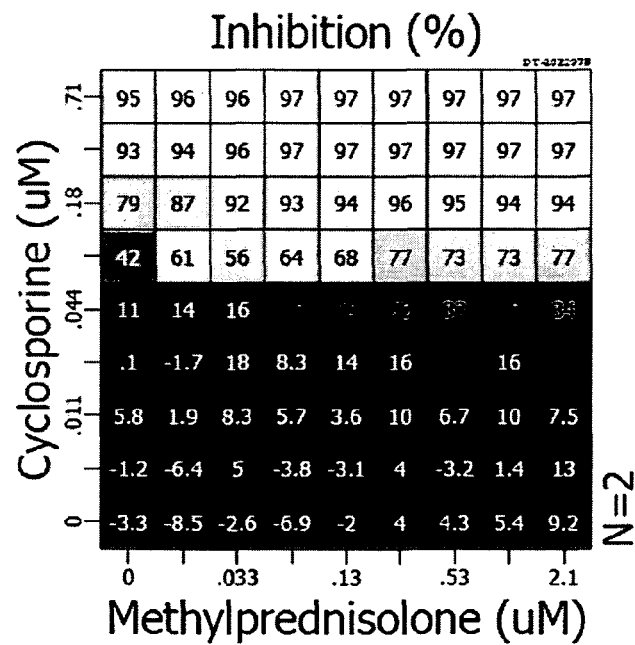
Fig. 1P. Methylprednisolone x Cyclosporine Anti-Inflammatory IL2 P/I PBMC Fig. 1Q. Methylprednisolone x Cyclosporine Anti-Inflammatory TNF Alpha P/I PBMC
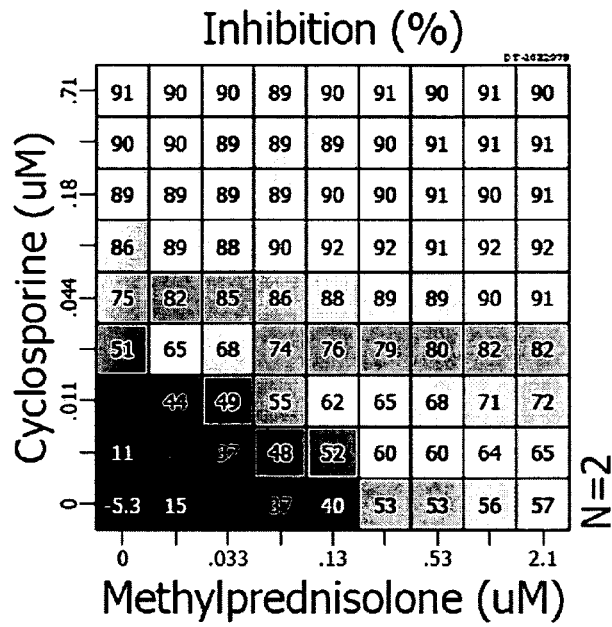
Fig. 1R. Methylprednisolone x Cyclosporine Anti-Inflammatory IFN Gamma P/I PBMC
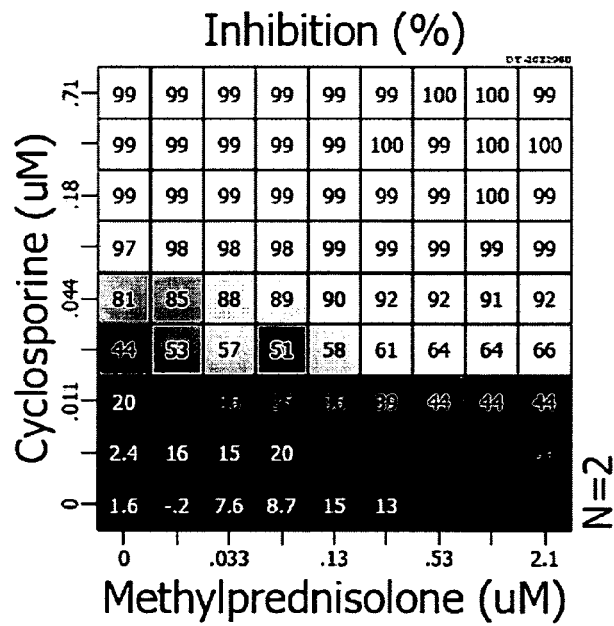

Fig. 1S. Prednisolone x Cyclosporine Anti-Inflammatory IL2 P/I PBMC
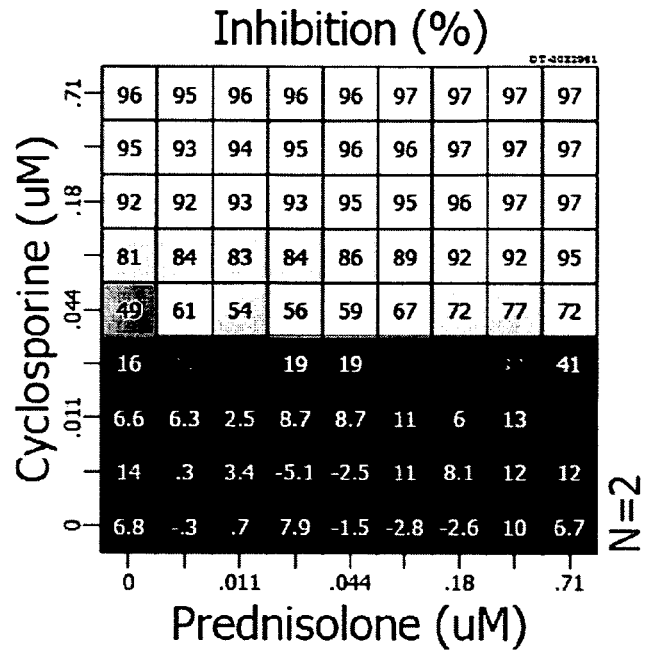
Fig. 1T. Prednisolone x Cyclosporine Anti-Inflammatory TNF Alpha P/I PBMC
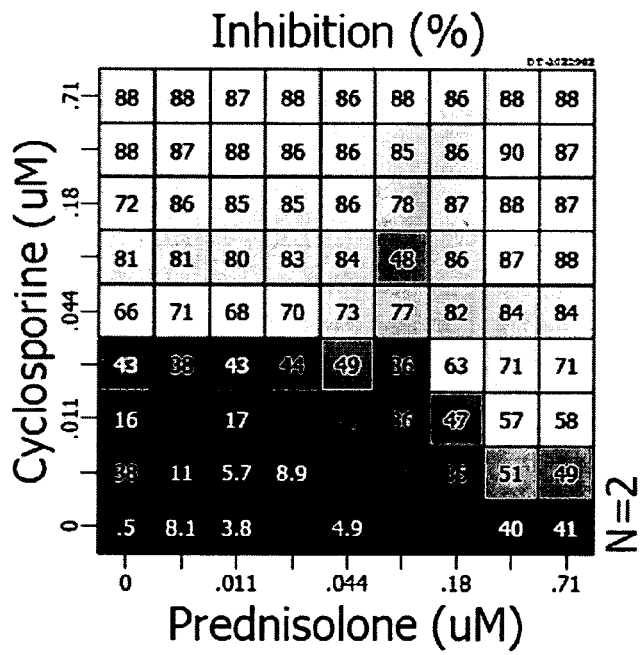

Fig. 1U. Prednisolone x Cyclosporine Anti-Inflammatory IFN Gamma P/I PBMC
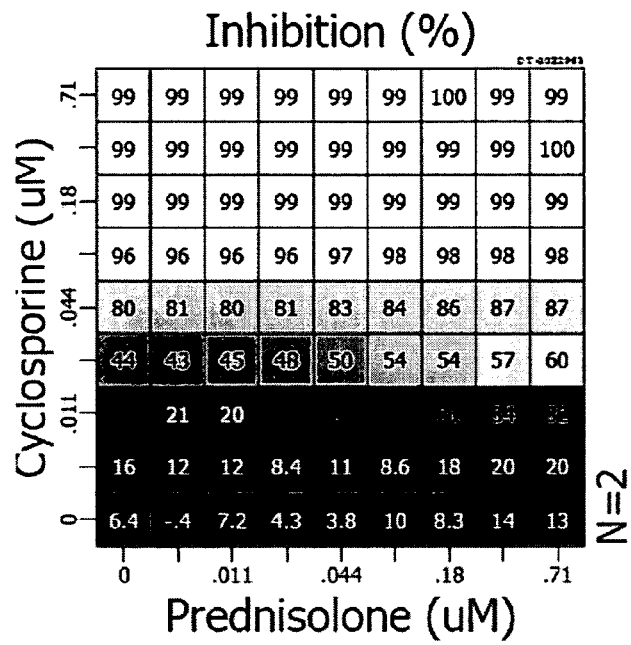
Fig. 1V. Prednisolone Acetate x Cyclosporine Anti-Inflammatory IL2 P/I PBMC
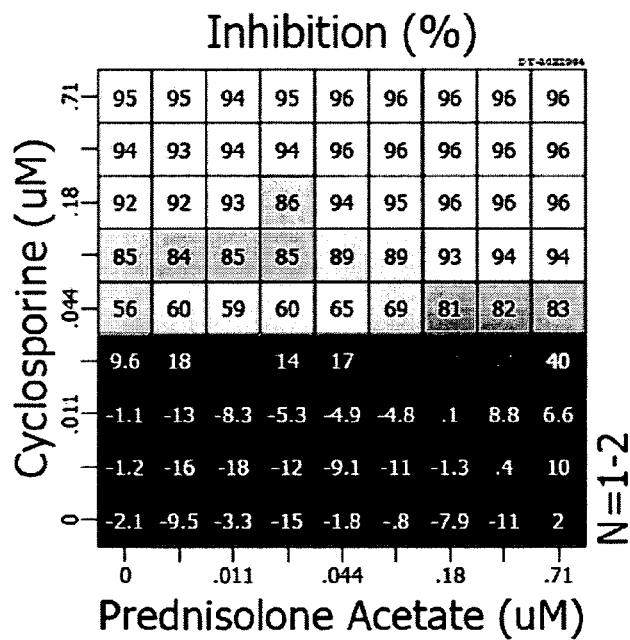

Fig. 1W. Prednisolone Acetate x Cyclosporine Anti-Inflammatory TNF Alpha P/I PBMC
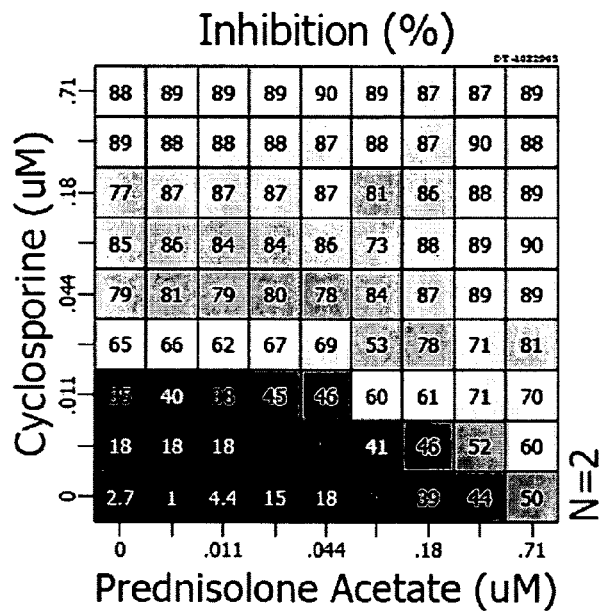
Fig. 1X. Prednisolone Acetate x Cyclosporine Anti-Inflammatory IFN Gamma P/I PBMC
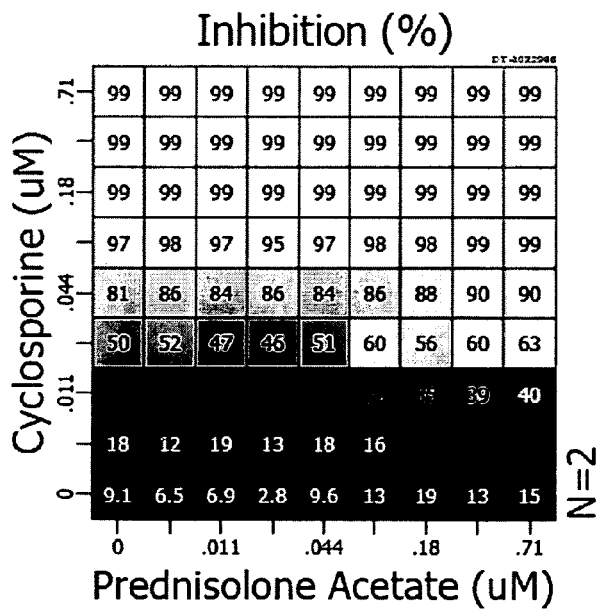

Fig. 1Y. Rimexolone x Cyclosporine Anti-Inflammatory IL2 P/I PBMC
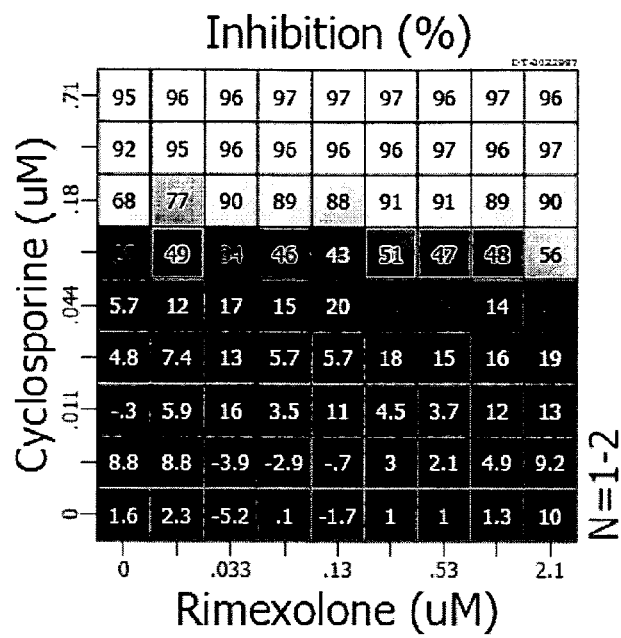
Fig. 1Z. Rimexolone x Cyclosporine Anti-Inflammatory TNF Alpha P/I PBMC
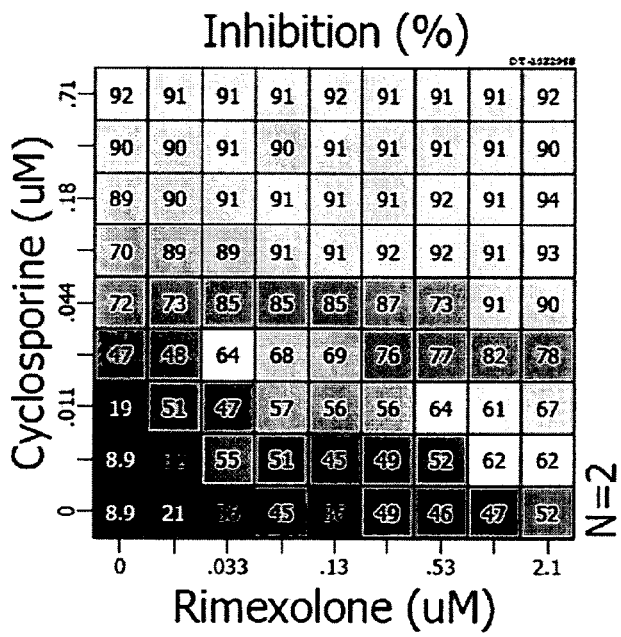

Fig. 1AA. Rimexolone x Cyclosporine Anti-Inflammatory IFN Gamma P/I PBMC
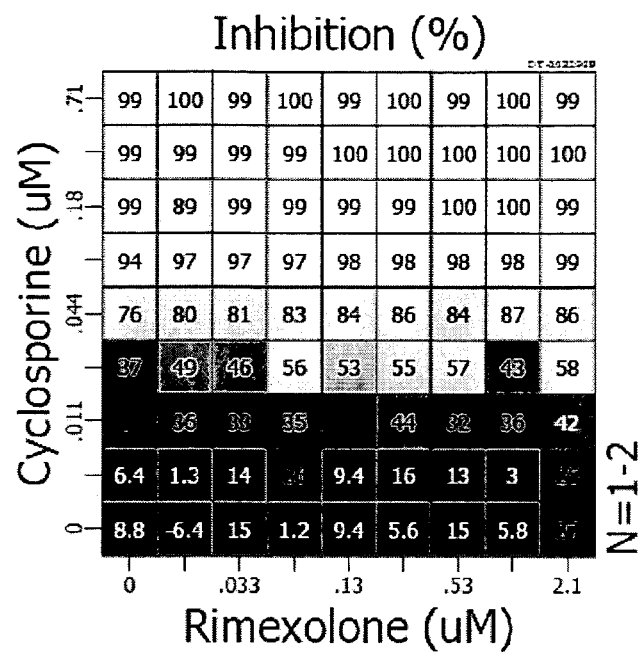
Fig. 1BB. Triamcinolone x Cyclosporine Anti-Inflammatory IL2 P/I PBMC
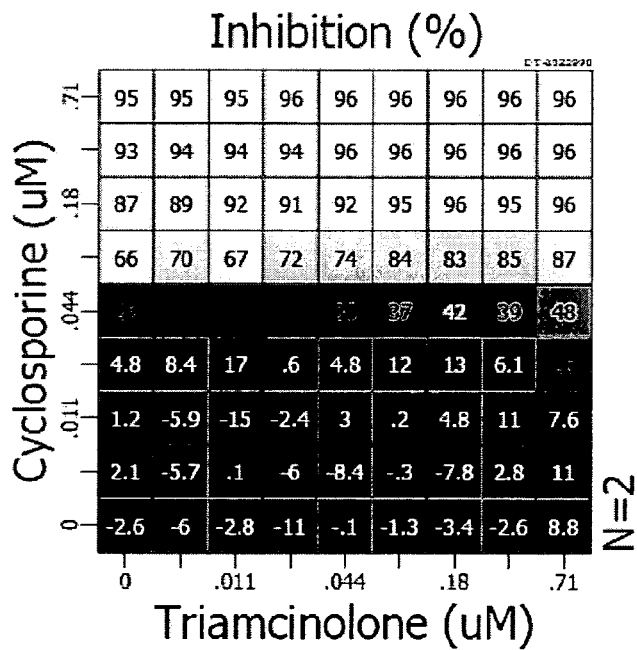

Fig. 1CC. Triamcinolone x Cyclosporine Anti-Inflammatory TNF Alpha P/I PBMC
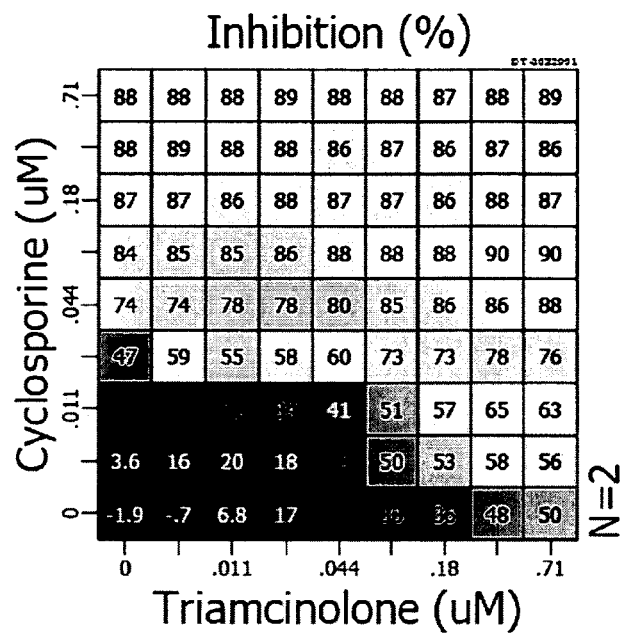
Fig. 1DD. Triamcinolone x Cyclosporine Anti-Inflammatory IFN Gamma P/I PBMC
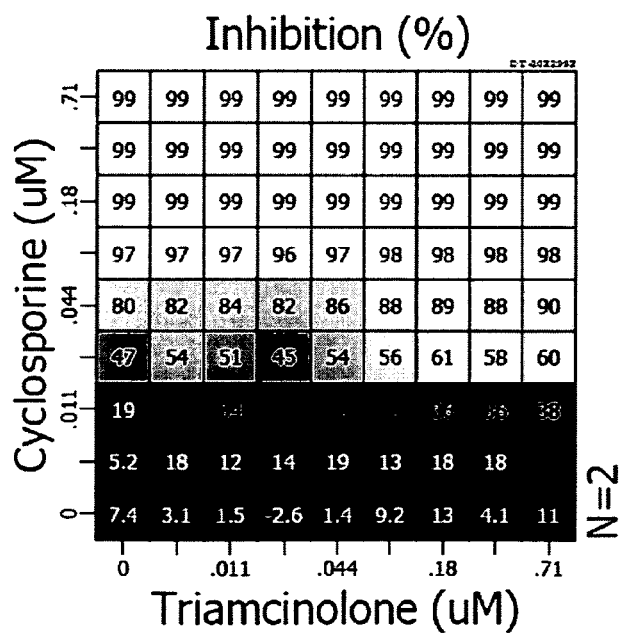

Fig. 1EE. Tacrolimus (FK-506) x Dexamethasone Anti-Inflammatory IL2 P/I PBMC
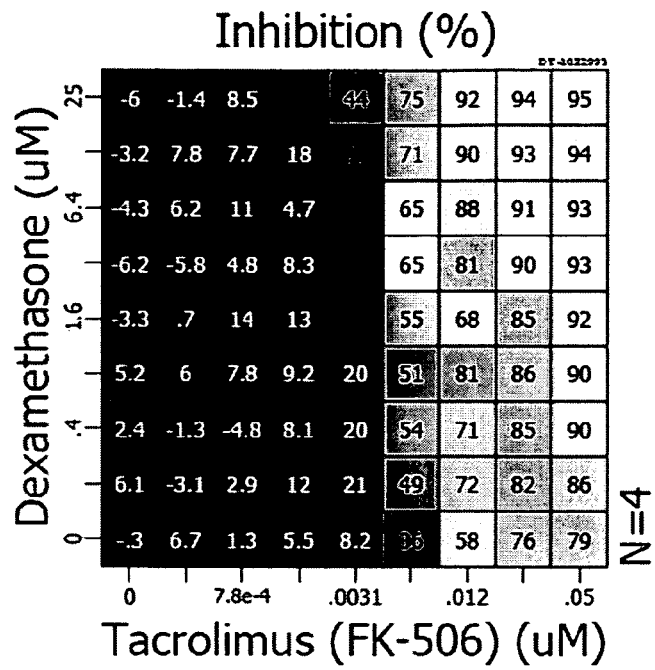
Fig. 1FF. Tacrolimus (FK-506) x Fluorometholone Anti-Inflammatory IL2 P/I PBMC
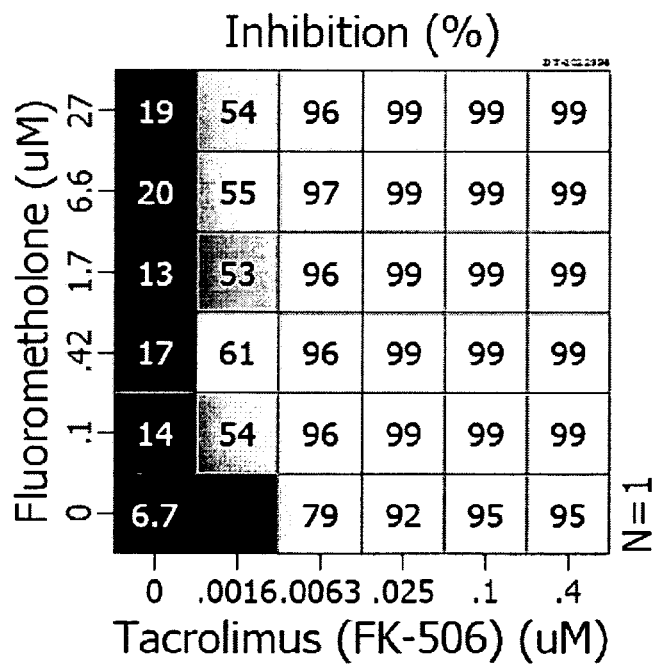

Fig. 1GG. Tacrolimus (FK-506) x Hydrocortisone Anti-Inflammatory IL2 P/I PBMC
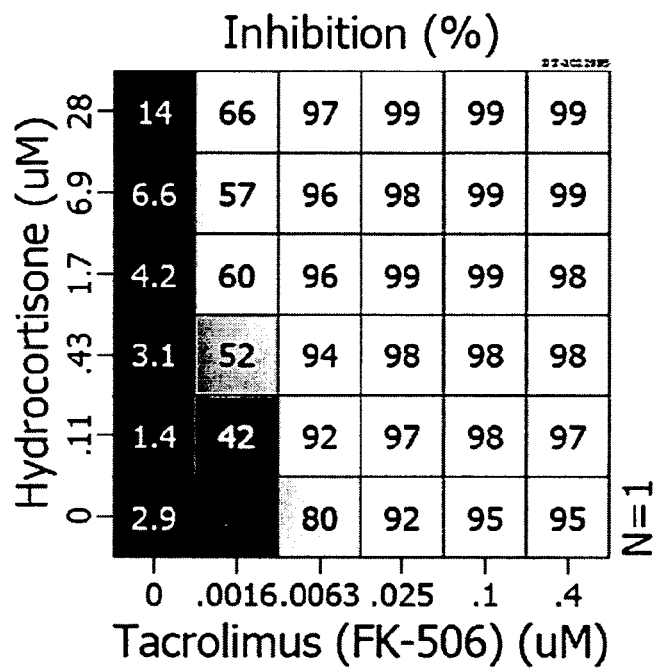
Fig. 1HH. Tacrolimus (FK-506) x Medrysone Anti-Inflammatory IL2 P/I PBMC
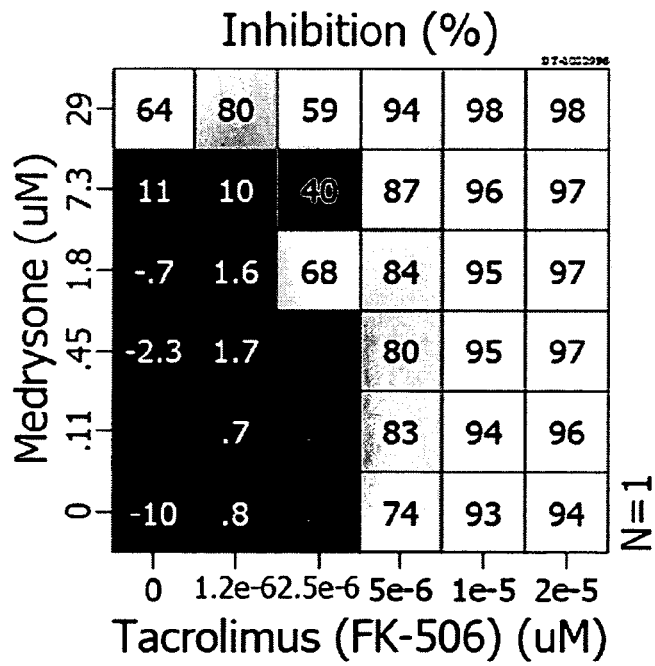

Fig. 1II. Tacrolimus (FK-506) x Methylprednisolone Anti-Inflammatory IL2 P/I PBMC
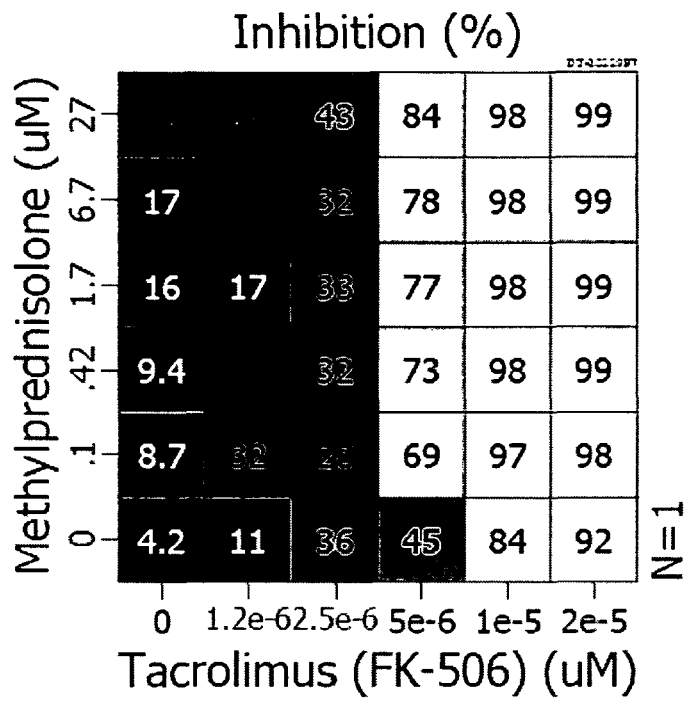
Fig. 1JJ. Tacrolimus (FK-506) x Prednisolone Acetate Anti-Inflammatory IL2 P/I PBMC
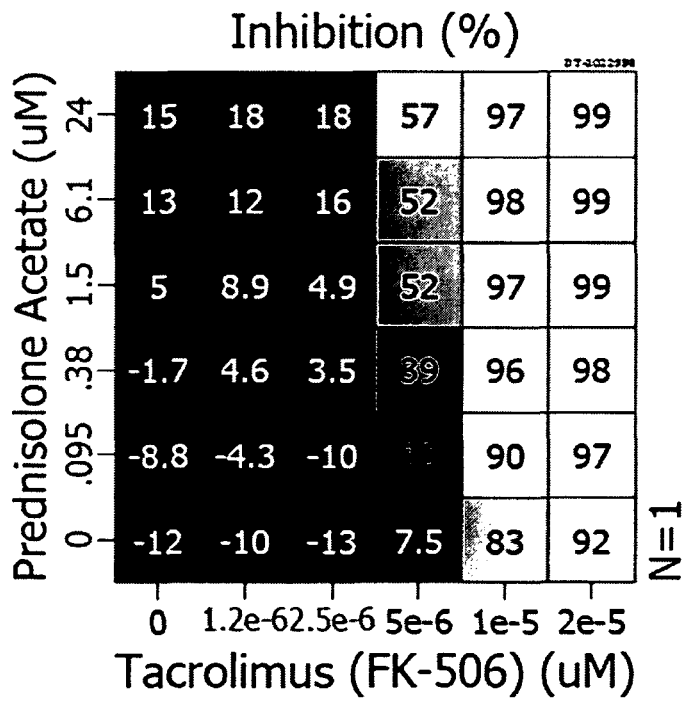

Fig. 1KK. Tacrolimus (FK-506) x Prednisolone Anti-Inflammatory IL2 P/I PBMC
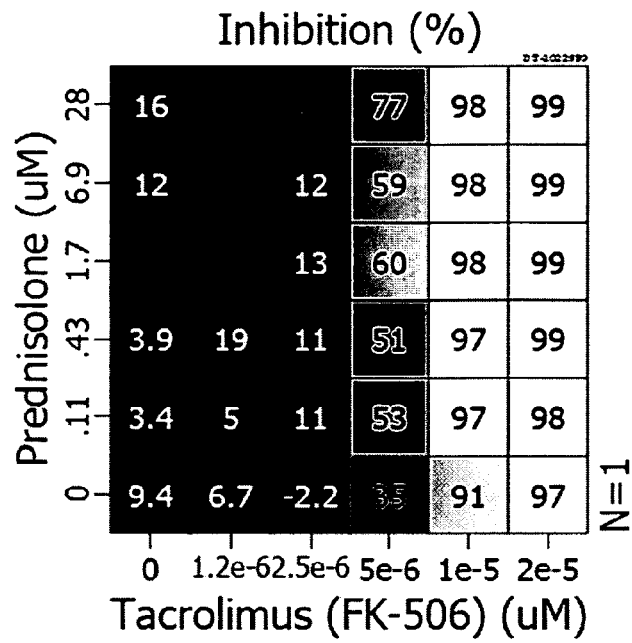
Fig. 1LL. Triamcinolone x Tacrolimus (FK-506) Anti-Inflammatory IL2 P/I PBMC
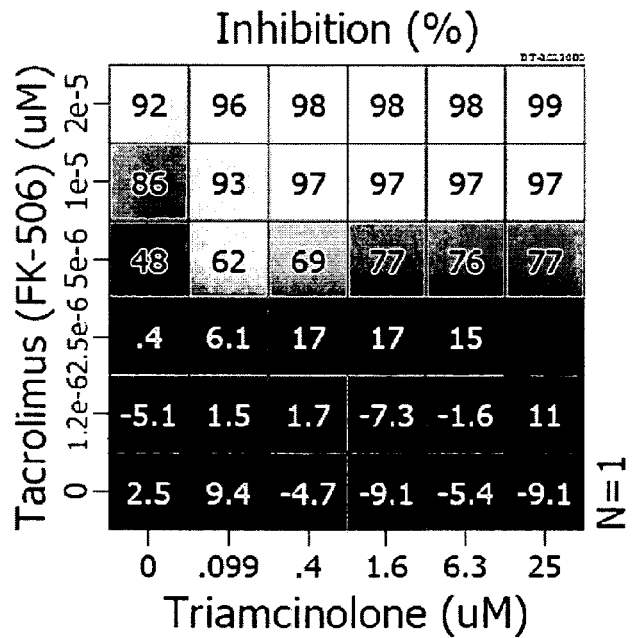

METHODS, COMPOSITIONS, AND KITS FOR THE TREATMENT OF OPHTHALMIC DISORDERS

CROSS-REFERENCE TO RELATED APPLICATIONS

This application claims benefit of U.S. Provisional Application No. 60/735,989, filed Nov. 9, 2005, which is hereby incorporated by reference.

BACKGROUND OF THE INVENTION

The invention relates to the treatment of ophthalmic disorders.

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid, manifest dry eye complications.

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

SUMMARY OF THE INVENTION

The invention features compositions, methods, and kits for the treatment of ophthalmic disorders.

In one aspect, the invention features a method of treating an ophthalmic disorder in a patient by administering to the patient a corticosteroid and a non-steroidal immunophilin-dependent immunosuppressant (NsIDI). In this aspect of the invention, the corticosteroid and/or the non-steroidal immunophilin-dependent immunosuppressant can be administered at a low concentration. Desirably, the concentration of the non-steroidal immunophilin-dependent immunosuppressant does not cause eye irritation, such as burning, and the compositions of the invention are administered in an amount sufficient to alleviate the symptoms of the ophthalmic disorder. Also desirably, the concentration of the corticosteroid does not cause steroid toxicity.

In another aspect, the invention features a method of treating an ophthalmic disorder in a patient by administering to the patient a substance selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents in combination with a corticosteroid and/or an NsIDI. In this aspect of the invention, the corticosteroid and/or the non-steroidal immunophilin-dependent immunosuppressant can be administered at a low concentration.

In another aspect, the invention features a composition (e.g., a solution, gel, ointment, suspension, emulsion, or solid insert) including a corticosteroid and a NsIDI. In this aspect of the invention, the corticosteroid and/or the NsIDI can be administered at a low concentration.

In another aspect, the invention features a composition (e.g., a solution, gel, ointment, suspension, emulsion, or solid insert) including a substance selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents in combination with a corticosteroid and/or an NsIDI. In this aspect of the invention, the corticosteroid and/or the non-steroidal immunophilin-dependent immunosuppressant can be administered at a low concentration.

The invention also features a kit that includes (i) a corticosteroid; and (ii) instructions for administering a corticosteroid and an NsIDI to a patient having or at risk of having an ophthalmic disorder.

The invention also features a kit that includes (i) an NsIDI; and (ii) instructions for administering a corticosteroid and an NsIDI to a patient having or at risk of having an ophthalmic disorder.

The invention also features a kit that includes (i) a composition containing a corticosteroid and an NsIDI; and (ii) instructions for administering the composition to a patient having or at risk of having a metabolic disorder.

The invention also features a kit that includes (i) a corticosteroid; (ii) an NsIDI; and (iii) instructions for administering a corticosteroid and an NsIDI to a patient having or at risk of having an ophthalmic disorder.

Any of the foregoing kits can also include instructions for administering a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents.

Any of the foregoing kits can also include a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents. In these kits, the NsIDI and/or corticosteroid can optionally be formulated in a single composition with a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents.

The invention also features a kit that includes (i) a corticosteroid; and (ii) instructions for administering a corticosteroid and a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents, to a patient having or at risk of having an ophthalmic disorder.

The invention also features a kit that includes (i) an NsIDI; and (ii) instructions for administering an NsIDI and a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents, to a patient having or at risk of having an ophthalmic disorder.

The invention also features a kit that includes (i) a composition containing a corticosteroid and a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents; and (ii) instructions for administering the composition to a patient having or at risk of having a metabolic disorder.

The invention also features a kit that includes (i) a composition containing an NsIDI and a compound selected from:

dipivefrin, anti-VEGF therapies, photodynamic therapy, NSAIDS, antiallergic agents, antihistamines, glaucoma-treating agents, artificial tears, antibiotics, antiviral agents, and antimycotic agents; and (ii) instructions for administering the composition to a patient having or at risk of having a metabolic disorder.

The invention also features a kit that includes (i) a corticosteroid; (ii) a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents (iii) instructions for administering a corticosteroid and a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents, to a patient having or at risk of having an ophthalmic disorder.

The invention also features a kit that includes (i) a NsIDI; (ii) a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents (iii) instructions for administering a NsIDI and a compound selected from: dipivefrin, anti-VEGF therapies, photodynamic therapy, NSAIDS, antiallergic agents, antihistamines, glaucoma-treating agents, artificial tears, antibiotics, antiviral agents, and antimycotic agents, to a patient having or at risk of having an ophthalmic disorder.

In any of the forgoing aspects of the invention, the corticosteroid can be selected from SEGRAs (selective glucocorticosteroid receptor agonists), fluocinolone acetonide, fluorometholone, dexamethasone, hydrocortisone, loteprednol, medrysone, methylprednisolone, prednisolone, rimexolone, or triamcinolone.

In any of the forgoing aspects of the invention, the NsIDI can be selected from cyclosporine A, ABT-281, ISAtx247, tacrolimus, ascomycin, pimecrolimus, rapamycin, or everolimus.

In any of the foregoing aspects of the invention, the concentration of the corticosteroid can be equivalent to a concentration of prednisolone of between 0.01% and 0.1% (e.g., 0.1%, 0.09%, 0.08%, 0.07%, 0.06%, 0.05%, or 0.01%) and the concentration of the non-steroidal immunophilin-dependent immunosuppressant can be equivalent to a concentration of cyclosporine A between 0.001% and 0.049% (e.g., 0.04%, 0.03%, 0.02%, 0.01%, 0.009%, 0.008%, 0.007%, 0.006%, 0.005%, or 0.001%).

In one embodiment, the corticosteroid is prednisolone and the concentration of prednisolone is between 0.01% and 0.12% (e.g., 0.12%, 0.1%, 0.09%, 0.08%, 0.07%, 0.06%, 0.05%, and 0.01%).

In another embodiment, the corticosteroid is clocortolone pivalate and the concentration of clocortolone pivalate is between 0.01% and 0.1% (e.g., 0.1%, 0.09%, 0.08%, 0.07%, 0.06%, 0.05%, and 0.01%).

In another embodiment, the corticosteroid is hydrocortisone and the concentration of hydrocortisone is between 0.01% and 1.0% (e.g., 1.0%, 0.9%, 0.8%, 0.7%, 0.6%, 0.5%, 0.1%, 0.09%, 0.08%, 0.07%, 0.06%, 0.05%, and 0.01%).

In another embodiment, the corticosteroid is dexamethasone and the concentration of dexamethasone is between 0.01% and 0.1% (e.g., 0.1%, 0.09%, 0.08%, 0.07%, 0.06%, 0.05%, and 0.01%).

In another embodiment, the corticosteroid is fluorometholone and the concentration of fluorometholone is between 0.01% and 0.1% (e.g., 0.1%, 0.09%, 0.08%, 0.07%, 0.06%, 0.05%, and 0.01%).

In another embodiment, the corticosteroid is loteprednol etabonate and the concentration of loteprednol etabonate is between 0.01% and 0.2% (e.g., 0.2%, 0.1%, 0.09%, 0.08%, 0.07%, 0.06%, 0.05%, and 0.01%).

In another embodiment, the corticosteroid is medrysone and the concentration of medrysone is between 0.01% and 1.0% (e.g., 1.0%, 0.9%, 0.8%, 0.7%, 0.6%, 0.5%, 0.1%, 0.09%, 0.08%, 0.07%, 0.06%, 0.05%, and 0.01%).

In another embodiment, the corticosteroid is rimexolone and the concentration of rimexolone is between 0.01% and 1.0% (e.g., 1.0%, 0.9%, 0.8%, 0.7%, 0.6%, 0.5%, 0.1%, 0.09%, 0.08%, 0.07%, 0.06%, 0.05%, and 0.01%).

In any of the foregoing embodiments, the non-steroidal immunophilin-dependent immunosuppressant is cyclosporine A and the concentration of cyclosporine A is between 0.001% and 0.049% (e.g., 0.04%, 0.03%, 0.02%, 0.01%, 0.009%, 0.008%, 0.007%, 0.006%, 0.005%, and 0.001%).

In certain embodiments of the compositions, kits, and methods of the invention, the only pharmacologically active agents in the composition or kit, or used in the method, are those recited. In this embodiment, pharmacologically inactive excipients may also be present in the composition or kit, or used in the practice of the method.

The invention features the treatment of an ophthalmic disorder, for example age related macular degeneration, alkaline erosive keratoconjunctivitis, allergic conjunctivitis, allergic keratitis, anterior uveitis, Behcet's disease, blepharitis, blood-aqueous barrier disruption, chorioiditis, chronic uveitis, conjunctivitis, contact lens-induced keratoconjunctivitis, corneal abrasion, corneal trauma, corneal ulcer, crystalline retinopathy, cystoid macular edema, dacryocystitis, diabetic keratophathy, diabetic macular edema, diabetic retinopathy, dry eye disease, dry age-related macular degeneration, eosinophilic granuloma, episcleritis, exudative macular edema, Fuchs' Dystrophy, giant cell arteritis, giant papillary conjunctivitis, glaucoma, glaucoma surgery failure, graft rejection, herpes zoster, inflammation after cataract surgery, iridocorneal endothelial syndrome, iritis, keratoconjunctiva sicca, keratoconjunctival inflammatory disease, keratoconus, lattice dystrophy, map-dot-fingerprint dystrophy, necrotic keratitis, neovascular diseases involving the retina, uveal tract or cornea such as neovascular glaucoma, corneal neovascularization, neovascularization resulting following a combined vitrectomy and lensectomy, neovascularization of the optic nerve, and neovascularization due to penetration of the eye or contusive ocular injury, neuroparalytic keratitis, non-infectious uveitisocular herpes, ocular lymphoma, ocular rosacea, ophthalmic infections, ophthalmic pemphigoid, optic neuritis, panuveitis, papillitis, pars planitis, persistent macular edema, phacoanaphylaxis, posterior uveitis, post-operative inflammation, proliferative diabetic retinopathy, proliferative sickle cell retinopathy, proliferative vitreoretinopathy, retinal artery occlusion, retinal detachment, retinal vein occlusion, retinitis pigmentosa, retinopathy of prematurity, rubeosis iritis, scleritis, Stevens-Johnson syndrome, sympathetic ophthalmia, temporal arteritis, thyroid associated ophthalmopathy, uveitis, vernal conjunctivitis, vitamin A insufficiency-induced keratomalacia, vitreitis, or wet age-related macular degeneration.

Compounds useful in the invention include those described herein in any of their pharmaceutically acceptable forms, including isomers such as diastereomers and enantiomers, salts, esters, solvates, and polymorphs thereof, as well as racemic mixtures and pure isomers of the compounds described herein.

By "corticosteroid" is meant any naturally occurring or synthetic compound characterized by a hydrogenated cyclopentanoperhydro-phenanthrene ring system and having immunosuppressive and/or anti-inflammatory activity. Naturally occurring corticosteroids are generally produced by the adrenal cortex. Synthetic corticosteroids may be halogenated. Examples corticosteroids are provided herein.

By "non-steroidal immunophilin-dependent immunosuppressant" or "NsIDI" is meant any non-steroidal agent that decreases proinflammatory cytokine production or secretion, binds an immunophilin, or causes a down regulation of the proinflammatory reaction. NsIDIs include calcineurin inhibitors, such as cyclosporine A, ABT-281, ISAtx247, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which bind to an FK506-binding protein, FKBP-12, and block antigen-induced proliferation of white blood cells and cytokine secretion.

By a "low dosage" or "low concentration" is meant at least 5% less (e.g., at least 10%, 20%, 50%, 80%, 90%, or even 95%) than the lowest standard recommended dosage or lowest standard recommended concentration (e.g., less than the concentration approved by the FDA for ophthalmic administration, see Table 1) of a particular compound formulated for a given route of administration for treatment of any human disease or condition. For example, a low dosage of corticosteroid formulated for administration by inhalation will differ from a low dosage of corticosteroid formulated for oral administration of a particular compound formulated for a given route of administration for treatment of any human disease or condition.

By "treating" is meant administering or prescribing a pharmaceutical composition for the treatment or prevention of an immunoinflammatory disease.

By "patient" is meant any animal (e.g., a human). Other animals that can be treated using the methods, compositions, and kits of the invention include horses, dogs, cats, pigs, goats, rabbits, hamsters, monkeys, guinea pigs, rats, mice, lizards, snakes, sheep, cattle, fish, and birds.

By a "concentration equivalent to a concentration of prednisolone" is meant a concentration of a corticosteroid that produces the same anti-inflammatory effect in a patient as a concentration of prednisolone.

By a "concentration equivalent to a concentration of cyclosporine A" is meant a concentration of a NsIDI that produces the same anti-inflammatory effect in a patient as a concentration of cyclosporine A.

"Ophthalmic disorder" refers to physiologic abnormalities of the eye. They may involve the retina, the vitreous humor, lens, cornea, sclera or other portions of the eye, or physiologic abnormalities that adversely affect the eye, such as inadequate tear production, allergic conjunctivitis, uveitis or corneal transplant.

By "steroid toxicity" is meant a detrimental increase in intraocular pressure resulting from steroid administration.

Ophthalmic disorders that can be treated using the compositions, methods, and kits of the invention include age related macular degeneration; alkaline erosive keratoconjunctivitis; allergic conjunctivitis; allergic keratitis; anterior uveitis (iridocyclitis); Behcet's disease; blepharitis; blood-aqueous barrier disruption; chorioiditis; chronic uveitis; conjunctivitis; contact lens-induced keratoconjunctivitis; corneal abrasion; corneal trauma; corneal ulcer (e.g., Mooren's ulcer, corneal ulcer subsequent to chronic rheumatoid arthritis or collagen disease, Terrien' margine degeneration, catarrhal corneal ulcer, infectious corneal ulcer); crystalline retinopathy; cystoid macular edema; dacryocystitis; diabetic keratophathy; diabetic macular edema; diabetic retinopathy; dry eye disease; dry age-related macular degeneration; eosinophilic granuloma; episcleritis; exudative macular edema; Fuchs' Dystrophy; giant cell arteritis; giant papillary conjunctivitis; glaucoma; glaucoma surgery failure; graft rejection; herpes zoster (shingles); inflammation after cataract surgery; iridocorneal endothelial syndrome; iritis; keratoconjunctiva sicca; keratoconjunctival inflammatory disease; keratoconus; lattice dystrophy; map-dot-fingerprint dystrophy; necrotic keratitis; neovascular diseases involving the retina, uveal tract or cornea such as neovascular glaucoma, corneal neovascularization (inflammatory, transplantation, developmental hypoplasia of the iris), neovascularization resulting following a combined vitrectomy and lensectomy, neovascularization of the optic nerve, and neovascularization due to penetration of the eye or contusive ocular injury; neuroparalytic keratitis; non-infectious uveitisocular herpes; ocular lymphoma; ocular rosacea; ophthalmic infections (e.g., corneal herpes, bacterial keratitis, bacterial conjunctivitis, mycotic keratitis, acanthamebic keratitis, infectious endophthalmitis, infectious corneal ulcer, inflammation of the conjunctiva or cornea by *staphylococci, streptococci, enterococci, euterococci, bacillus, corynebacterium, chlamydia,* and *neisseria*); ophthalmic pemphigoid; optic neuritis; panuveitis; papillitis; pars planitis; persistent macular edema; phacoanaphylaxis; posterior uveitis (chorioentinitis); post-operative inflammation; proliferative diabetic retinopathy; proliferative sickle cell retinopathy; proliferative vitreoretinopathy; retinal artery occlusion; retinal detachment; retinal vein occlusion; retinitis pigmentosa; retinopathy of prematurity; rubeosis iritis; scleritis; Stevens-Johnson syndrome (erythema multiforme major); sympathetic ophthalmia; temporal arteritis; thyroid associated ophthalmopathy (Graves' Ophthalmopathy); uveitis; vernal conjunctivitis; vitamin A insufficiency-induced keratomalacia; vitreitis; and wet age-related macular degeneration.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds useful in the invention include those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein.

Other features and advantages of the invention will be apparent from the following detailed description.

BRIEF DESCRIPTION OF THE DRAWINGS

FIGS. 1A-1LL are graphs showing suppression of IFNγ, IL-2, and TNFα in cells treated with combinations of an NsIDI and a corticosteroid.

DETAILED DESCRIPTION

The invention features methods, compositions, and kits for the treatment of ophthalmic disorders. In one embodiment, a patient with an ophthalmic disorder is treated by administering two drugs simultaneously.

Cyclosporine A, a non-steroidal immunophilin-dependent immunosuppressant (NsIDI), is approved for treating several ophthalmic conditions. Cyclosporine A causes eye irritation and other undesired side effects when administered to patients at the lowest approved concentration. Lower concentrations of cyclosporine A do not cause these undesired side effects but are not sufficient to alleviate the symptoms of the ophthalmic disorders.

Both corticosteroids and NsIDIs suppress cytokine production in cell culture models of immune function. We have discovered that combinations of certain NsIDIs with certain corticosteroids suppress cytokine production in a synergistic manner.

Based upon these data, we propose that when combined with a corticosteroid, low concentrations of cyclosporine A are sufficient to alleviate the symptoms of ophthalmic disorders while not causing undesired side effects.

Corticosteroids

In certain embodiments, a corticosteroid may be employed in a method, composition, or kit of the invention. Suitable corticosteroids include those from the class of selective glucocorticosteroid receptor agonists (SEGRAs), 11-alpha,17-alpha,21-trihydroxypregn-4-ene-3,20-dione; 11-beta,16-alpha,17,21-tetrahydroxypregn-4-ene-3,20-dione; 11-beta,16-alpha,17,21-tetrahydroxypregn-1,4-diene-3,20-dione; 11-beta,17-alpha,21-trihydroxy-6-alpha-methylpregn-4-ene-3,20-dione; 11-dehydrocorticosterone; 11-deoxycortisol; 11-hydroxy-1,4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)-triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-acetoxypregnenolone; 21-deoxyaldosterone; 21-deoxycortisone; 2-deoxyecdysone; 2-methylcortisone; 3-dehydroecdysone; 4-pregnene-17-alpha,20-beta, 21-triol-3,11-dione; 6,17,20-trihydroxypregn-4-ene-3-one; 6-alpha-hydroxycortisol; 6-alpha-fluoroprednisolone, 6-alpha-methylprednisolone, 6-alpha-methylprednisolone 21-acetate, 6-alpha-methylprednisolone 21-hemisuccinate sodium salt, 6-beta-hydroxycortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclomethasone dipropionate; aldosterone; algestone; alphaderm; amadinone; amcinonide; anagestone; androstenedione; anecortave acetate; beclomethasone; beclomethasone dipropionate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; ciclesonide; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortivazol; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; difluprednate; dihydroelatericin a; domoprednate; doxibetasol; ecdysone; ecdysterone; emoxolone; endrysone; enoxolone; fluazacort; flucinolone; flucloronide; fludrocortisone; fludrocortisone acetate; flugestone; flumethasone; flumethasone pivalate; flumoxonide; flunisolide; fluocinolone; fluocinolone acetonide; fluocinonide; fluocortin butyl; 9-fluorocortisone; fluocortolone; fluorohydroxyandrostenedione; fluorometholone; fluorometholone acetate; fluoxymesterone; fluperolone acetate; fluprednidene; fluprednisolone; flurandrenolide; fluticasone; fluticasone propionate; formebolone; formestane; formocortal; gestonorone; glyderinine; halcinonide; halobetasol propionate; halometasone; halopredone; haloprogesterone; hydrocortamate; hydrocortiosone cypionate; hydrocortisone; hydrocortisone 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; loteprednol etabonate; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednicarbate; prednisolamate; prednisolone; prednisolone 21-diethylaminoacetate; prednisolone 21-hemisuccinate; prednisolone acetate; prednisolone farnesylate; prednisolone hemisuccinate; prednisolone-21 (beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone benetonide; triamcinolone diacetate; triamcinolone hexacetonide; trimegestone; turkesterone; and wortmannin.

Steroid Receptor Modulators

Steroid receptor modulators (e.g., antagonists and agonists) may be used as a substitute for or in addition to a corticosteroid in the methods, compositions, and kits of the invention. Glucocorticoid receptor modulators that may used in the methods, compositions, and kits of the invention include compounds described in U.S. Pat. Nos. 6,380,207, 6,380,223, 6,448,405, 6,506,766, and 6,570,020, U.S. Patent Application Publication Nos. 2003/0176478, 2003/0171585, 2003/0120081, 2003/0073703, 2002/015631, 2002/0147336, 2002/0107235, 2002/0103217, and 2001/0041802, and PCT Publication No. WO00/66522, each of which is hereby incorporated by reference. Other steroid receptor modulators may also be used in the methods, compositions, and kits of the invention are described in U.S. Pat. Nos. 6,093,821, 6,121,450, 5,994,544, 5,696,133, 5,696,127, 5,693,647, 5,693,646, 5,688,810, 5,688,808, and 5,696,130, each of which is hereby incorporated by reference.

Other Compounds

Other compounds that may be used as a substitute for or in addition to a corticosteroid in the methods, compositions, and kits of the invention A-348441 (Karo Bio), adrenal cortex extract (GlaxoSmithKline), alsactide (Aventis), amebucort (Schering AG), amelometasone (Taisho), ATSA (Pfizer), bitolterol (Elan), CBP-2011 (InKine Pharmaceutical), cebaracetam (Novartis) CGP-13774 (Kissei), ciclesonide (Altana), ciclometasone (Aventis), clobetasone butyrate (GlaxoSmithKline), cloprednol (Hoffmann-La Roche), collismycin A (Kirin), cucurbitacin E (NIH), deflazacort (Aventis), deprodone propionate (SSP), dexamethasone acefurate (Schering-Plough), dexamethasone linoleate (GlaxoSmithKline), dexamethasone valerate (Abbott), difluprednate (Pfizer), domoprednate (Hoffmann-La Roche), ebiratide (Aventis), etiprednol dicloacetate (IVAX), fluazacort (Vicuron), flumoxonide (Hoffmann-La Roche), fluocortin butyl (Schering AG), fluocortolone monohydrate (Schering AG), GR-250495X (GlaxoSmithKline), halometasone (Novartis), halopredone (Dainippon), HYC-141 (Fidia), icomethasone enbutate (Hovione), itrocinonide (AstraZeneca), L-6485 (Vicuron), Lipocort (Draxis Health), locicortone (Aventis), meclorisone (Schering-Plough), naflocort (Bristol-Myers Squibb), NCX-1015 (NicOx), NCX-1020 (NicOx), NCX-1022 (NicOx), nicocortonide (Yamanouchi), NIK-236 (Nikken Chemicals), NS-126 (SSP), Org-2766 (Akzo Nobel), Org-6632 (Akzo Nobel), P16CM, propylmesterolone (Schering AG), RGH-1113 (Gedeon Richter), rofleponide (AstraZeneca), rofleponide palmitate (AstraZeneca), RPR-106541 (Aventis), RU-26559 (Aventis), Sch-19457 (Schering-Plough), T25 (Matrix Therapeutics), TBI-PAB (Sigma-Tau), ticabesone propionate (Hoffmann-La Roche), tifluadom (Solvay), timobesone (Hoffmann-La Roche), TSC-5 (Takeda), and ZK-73634 (Schering AG).

Non-Steroidal Immunophilin-Dependent Immunosuppressants

In certain embodiments, the invention features methods, compositions, and kits employing a non-steroidal immunophilin-dependent immunosuppressant (NsIDI).

In healthy individuals the immune system uses cellular effectors, such as B-cells and T-cells, to target infectious microbes and abnormal cell types while leaving normal cells intact. In individuals with an autoimmune disorder or a transplanted organ, activated T-cells damage healthy tissues. Calcineurin inhibitors (e.g., cyclosporines, tacrolimus, pimecrolimus, ABT-281, ISAtx247), and rapamycin target many types of immunoregulatory cells, including T-cells, and suppress the immune response in organ transplantation and autoimmune disorders.

Cyclosporines

The cyclosporines are fungal metabolites that comprise a class of cyclic oligopeptides that act as immunosuppressants.

Cyclosporine A is a hydrophobic cyclic polypeptide consisting of eleven amino acids. It binds and forms a complex with the intracellular receptor cyclophilin. The cyclosporine/cyclophilin complex binds to and inhibits calcineurin, a $Ca^{2+}$-calmodulin-dependent serine-threonine-specific protein phosphatase. Calcineurin mediates signal transduction events required for T-cell activation (reviewed in Schreiber et al., Cell 70:365-368, 1991). Cyclosporines and their functional and structural analogs suppress the T cell-dependent immune response by inhibiting antigen-triggered signal transduction. This inhibition decreases the expression of proinflammatory cytokines, such as IL-2.

Many different cyclosporines (e.g., cyclosporine A, B, C, D, E, F, G, H, and I) are produced by fungi. Cyclosporine A is a commercially available under the trade name NEORAL from Novartis. Cyclosporine A structural and functional analogs include cyclosporines having one or more fluorinated amino acids (described, e.g., in U.S. Pat. No. 5,227,467); cyclosporines having modified amino acids (described, e.g., in U.S. Pat. Nos. 5,122,511 and 4,798,823); and deuterated cyclosporines, such as ISAtx247 (described in U.S. Patent Application Publication No. 2002/0132763 A1). Additional cyclosporine analogs are described in U.S. Pat. Nos. 6,136,357, 4,384,996, 5,284,826, and 5,709,797. Cyclosporine analogs include, but are not limited to, D-Sar ($\alpha$-SMe)$^3$ Val$^2$-DH-Cs (209-825), Allo-Thr-2-Cs, Norvaline-2-Cs, D-Ala(3-acetylamino)-8-Cs, Thr-2-Cs, and D-MeSer-3-Cs, D-Ser(O-$CH_2CH_2$-OH)-8-Cs, and D-Ser-8-Cs, which are described in Cruz et al. (Antimicrob. Agents Chemother. 44:143-149, 2000).

Cyclosporines are highly hydrophobic and readily precipitate in the presence of water (e.g. on contact with body fluids). Methods of providing cyclosporine formulations with improved bioavailability are described in U.S. Pat. Nos. 4,388,307, 6,468,968, 5,051,402, 5,342,625, 5,977,066, and 6,022,852. Cyclosporine microemulsion compositions are described in U.S. Pat. Nos. 5,866,159, 5,916,589, 5,962,014, 5,962,017, 6,007,840, and 6,024,978.

Tacrolimus

Tacrolimus (FK506) is an immunosuppressive agent that targets T cell intracellular signal transduction pathways. Tacrolimus binds to an intracellular protein FK506 binding protein (FKBP-12) that is not structurally related to cyclophilin. The FKBP/FK506 complex binds to calcineurin and inhibits calcineurin's phosphatase activity. This inhibition prevents the dephosphorylation and nuclear translocation of nuclear factor of activated T cells (NFAT), a nuclear component that initiates gene transcription required for proinflammatory cytokine (e.g., IL-2, gamma interferon) production and T cell activation. Thus, tacrolimus inhibits T cell activation.

Tacrolimus is a macrolide antibiotic that is produced by *Streptomyces tsukubaensis*. It suppresses the immune system and prolongs the survival of transplanted organs. It is currently available in oral and injectable formulations. Tacrolimus capsules contain 0.5 mg, 1 mg, or 5 mg of anhydrous tacrolimus within a gelatin capsule shell. The injectable formulation contains 5 mg anhydrous tacrolimus in castor oil and alcohol that is diluted with 0.9% sodium chloride or 5% dextrose prior to injection. While oral administration is preferred, patients unable to take oral capsules may receive injectable tacrolimus. The initial dose should be administered no sooner than six hours after transplant by continuous intravenous infusion.

Tacrolimus and tacrolimus analogs are described by Tanaka et al. (J. Am. Chem. Soc., 109:5031, 1987) and in U.S. Pat. Nos. 4,894,366, 4,929,611, and 4,956,352. FK506-related compounds, including FR-900520, FR-900523, and FR-900525, are described in U.S. Pat. No. 5,254,562; O-aryl, O-alkyl, O-alkenyl, and O-alkynylmacrolides are described in U.S. Pat. Nos. 5,250,678, 532,248, 5,693,648; amino O-aryl macrolides are described in U.S. Pat. No. 5,262,533; alkylidene macrolides are described in U.S. Pat. No. 5,284,840; N-heteroaryl, N-alkylheteroaryl, N-alkenylheteroaryl, and N-alkynylheteroaryl macrolides are described in U.S. Pat. No. 5,208,241; aminomacrolides and derivatives thereof are described in U.S. Pat. No. 5,208,228; fluoromacrolides are described in U.S. Pat. No. 5,189,042; amino O-alkyl, O-alkenyl, and O-alkynylmacrolides are described in U.S. Pat. No. 5,162,334; and halomacrolides are described in U.S. Pat. No. 5,143,918.

Tacrolimus is extensively metabolized by the mixed-function oxidase system, in particular, by the cytochrome P-450 system. The primary mechanism of metabolism is demethylation and hydroxylation. While various tacrolimus metabolites are likely to exhibit immunosuppressive biological activity, the 13-demethyl metabolite is reported to have the same activity as tacrolimus.

Pimecrolimus

Pimecrolimus is the 33-epi-chloro derivative of the macrolactam ascomyin. Pimecrolimus structural and functional analogs are described in U.S. Pat. No. 6,384,073. Pimecrolimus is particularly useful for the treatment of atopic dermatitis. Pimecrolimus is currently available as a 1% cream.

Rapamycin

Rapamycin is a cyclic lactone produced by *Streptomyces hygroscopicus*. Rapamycin is an immunosuppressive agent that inhibits T cell activation and proliferation. Like cyclosporines and tacrolimus, rapamycin forms a complex with the immunophilin FKBP-12, but the rapamycin-FKBP-12 complex does not inhibit calcineurin phosphatase activity. The rapamycin immunophilin complex binds to and inhibits the mammalian kinase target of rapamycin (mTOR). mTOR is a kinase that is required for cell-cycle progression. Inhibition of mTOR kinase activity blocks T cell activation and proinflammatory cytokine secretion.

Rapamycin structural and functional analogs include mono- and diacylated rapamycin derivatives (U.S. Pat. No. 4,316,885); rapamycin water-soluble prodrugs (U.S. Pat. No. 4,650,803); carboxylic acid esters (PCT Publication No. WO 92/05179); carbamates (U.S. Pat. No. 5,118,678); amide esters (U.S. Pat. No. 5,118,678); biotin esters (U.S. Pat. No.5, 504,091); fluorinated esters (U.S. Pat. No. 5,100,883); acetals (U.S. Pat. No. 5,151,413); silyl ethers (U.S. Pat. No. 5,120, 842); bicyclic derivatives (U.S. Pat. No. 5,120,725); rapamycin dimers (U.S. Pat. No. 5,120,727); O-aryl, O-alkyl, O-alkyenyl and O-alkynyl derivatives (U.S. Pat. No. 5,258, 389); and deuterated rapamycin (U.S. Pat. No. 6,503,921). Additional rapamycin analogs are described in U.S. Pat. Nos. 5,202,332 and 5,169,851.

Peptide Moieties

Peptides, peptide mimetics, peptide fragments, either natural, synthetic or chemically modified, that impair the calcineurin-mediated dephosphorylation and nuclear translocation of NFAT are suitable for use in practicing the invention. Examples of peptides that act as calcineurin inhibitors by inhibiting the NFAT activation and the NFAT transcription factor are described, e.g., by Aramburu et al., Science 285: 2129-2133, 1999) and Aramburu et al., Mol. Cell 1:627-637, 1998). As a class of calcineurin inhibitors, these agents are useful in the methods, compositions, and kits of the invention.

Therapy

The invention features methods for treating an ophthalmic disorder. While the examples describe a two-drug combination, it is understood that the combination of multiple agents is often desirable. Additional therapies are described below.

Desirably, the methods, compositions, and kits of the invention are more effective than other methods, compositions, and kits. By "more effective" is meant that a method, composition, or kit exhibits greater efficacy, is less toxic, safer, more convenient, better tolerated, or less expensive, or provides more treatment satisfaction than another method, composition, or kit with which it is being compared.

Additional Compounds

Unless the intended purpose of use is affected adversely, the prophylactic and therapeutic medicament of the present invention may contain or may be used together with other appropriate pharmacologically effective substances. This includes the combination of a corticosteroid and NsIDI with other pharmacologically effective substances as well as either a corticosteroid or NsIDI with other pharmacologically effective substances. Exemplary pharmacologically effective substances are dipivefrin (e.g., dipivefrin hydrochloride ophthalmic 0.1%), anti-VEGF therapies (e.g., bevacizumab, pegaptanib (MACUGEN) ranibizumab, anecortave acetate, and squalamine lactate), photodynamic therapy (e.g., VISUDYNE (verteporfin)), NSAIDS (e.g., suprofen, indomethacin, flurbiprofen, ketorolac, diclofenac sodium, pranoprofen), antiallergic agents (e.g., ibudilast, tranilast, ketotifen fumarate, sodium cromoglicate, cromolyn sodium, nedocromil sodium, azelastine), antihistamines (e.g., epinastine, emedastine, levocabastine, olopatadine, diphenhydramine hydrochloride), glaucoma-treating agents (e.g., bimatoprost, apraclonidine, travoprost, latanoprost, brimonidine, pilocarpine hydrochloride, physostigmine salicylate, timolol, isopropylunoprostone), artificial tears, antibiotics (e.g., gentamycin sulfate, fradiomycin sulfate, tobramycin, sulbenicillin, cefmenoxime, erythromycin, colistin, oxytetracycline, polymyxin B, chloramphenicol, micronomicin, dibekacin, sisomicin, sulfamethizole, sulfamethoxazole, ofloxacin, norfloxacin, lomefloxacin hydrochloride, enoxacin, ciprofloxacin hydrochloride, cinoxacin, sparfloxacin, tosufloxacin tosylate, nalidixic acid, pipemidic acid trihydrate, pipemidic acid, fleroxacin, levofloxacin), antiviral agents (e.g., idoxuridine, acyclovir, ganciclovir), and antimycotic agents (e.g., pimaricin, fluconazole, miconazole, amphotericin B, flucytosine, itraconazole).

Ophthalmic Disorders

The methods, compositions, and kits of the invention may be used for the treatment of ophthalmic disorders. Examples of ophthalmic disorders are age related macular degeneration, alkaline erosive keratoconjunctivitis, allergic conjunctivitis, allergic keratitis, anterior uveitis, Behcet's disease, blepharitis, blood-aqueous barrier disruption, chorioiditis, chronic uveitis, conjunctivitis, contact lens-induced keratoconjunctivitis, corneal abrasion, corneal trauma, corneal ulcer, crystalline retinopathy, cystoid macular edema, dacryocystitis, diabetic keratophathy, diabetic macular edema, diabetic retinopathy, dry eye disease, dry age-related macular degeneration, eosinophilic granuloma, episcleritis, exudative macular edema, Fuchs' Dystrophy, giant cell arteritis, giant papillary conjunctivitis, glaucoma, glaucoma surgery failure, graft rejection, herpes zoster, inflammation after cataract surgery, iridocorneal endothelial syndrome, iritis, keratoconjunctiva sicca, keratoconjunctival inflammatory disease, keratoconus, lattice dystrophy, map-dot-fingerprint dystrophy, necrotic keratitis, neovascular diseases involving the retina, uveal tract or cornea such as neovascular glaucoma, corneal neovascularization, neovascularization resulting following a combined vitrectomy and lensectomy, neovascularization of the optic nerve, and neovascularization due to penetration of the eye or contusive ocular injury, neuroparalytic keratitis, non-infectious uveitisocular herpes, ocular lymphoma, ocular rosacea, ophthalmic infections, ophthalmic pemphigoid, optic neuritis, panuveitis, papillitis, pars planitis, persistent macular edema, phacoanaphylaxis, posterior uveitis, post-operative inflammation, proliferative diabetic retinopathy, proliferative sickle cell retinopathy, proliferative vitreoretinopathy, retinal artery occlusion, retinal detachment, retinal vein occlusion, retinitis pigmentosa, retinopathy of prematurity, rubeosis iritis, scleritis, Stevens-Johnson syndrome, sympathetic ophthalmia, temporal arteritis, thyroid associated ophthalmopathy, uveitis, vernal conjunctivitis, vitamin A insufficiency-induced keratomalacia, vitreitis, or wet age-related macular degeneration.

Administration

In particular embodiments of any of the methods of the invention, the compounds are administered within 14 days of each other, within 10 days of each other, within five days of each other, within twenty-four hours of each other, or simultaneously. The compounds may be formulated together as a single composition, or may be formulated and administered separately. One or both compounds may be administered in a low dosage or in a high dosage, each of which is defined herein. It may be desirable to administer to the patient other compounds, such as a humectant, NSAID (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, and tolmetin), COX-2 inhibitor (e.g., rofecoxib, celecoxib, valdecoxib, and lumiracoxib), glucocorticoid receptor modulator, or DMARD.

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and how the patient responds to the treatment. Additionally, a person having a greater risk of developing an ophthalmic disease (e.g., a person who is undergoing age-related hormonal changes) may receive treatment to inhibit or delay the onset of symptoms.

Each compound of the combination may be formulated in a variety of ways that are known in the art. For example, the first and second agents may be formulated together or separately. Desirably, the first and second agents are formulated together for the simultaneous or near simultaneous administration of the agents. Such co-formulated compositions can include the two drugs together in the same ointment, cream, foam, liquid, etc. By using different formulation strategies for different agents, the pharmacokinetic profiles for each agent can be suitably matched.

Ophthalmic Formulations

Ophthalmic formulations include but are not limited to ocular injections such as intravitreal, subtenons, subconjunctival, periocular, retrobulbar injections; topical ophthalmic aqueous solutions, such as suspensions, ointments, and gels; intraocular biodegradable and non-biodegradable implants; implants that are inserted through incisions made in the eye wall or sutured around the globe of the eye; tack for intraocular drug delivery; and bioadhesive ophthalmic inserts.

For topical ophthalmic administration of combinations of the invention, formulations may take the form of solutions, gels, ointments, suspensions or solid inserts, formulated so that a unit dosage comprises a therapeutically effective amount of each active component or some submultiple thereof.

Typical ophthalmologically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, benzalkonium chloride, methyl and propyl paraben, benzyldodecinium bromide, benzyl alcohol, phenylethanol, buffering ingredients such as sodium chloride, sodium borate, sodium acetate, or gluconate buffers, and other conventional ingredients such as sorbitan monolaurate, triethanolamine, polyoxyethylene sorbitan monopalmitylate, dioctyl sodium sulfosuccinate, monothioglycerol, thiosorbitol, ethylenediamine tetra-acetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The formulation may also include a gum such as gellan gum at a concentration of, for example, 0.1 to 2% by weight so that the aqueous eyedrops gel on contact with the eye, thus providing the advantages of a solid ophthalmic insert as described in U.S. Pat. No. 4,861,760.

The pharmaceutical preparation may also be in the form of a solid insert such as one which after dispensing the drug remains essentially intact as described in U.S. Pat. Nos. 4,256,108; 4,160,452; and 4,265,874; or a bio-erodible insert that either is soluble in lacrimal fluids, or otherwise disintegrates as described in U.S. Pat. No. 4,287,175 or EPO publication 0077261.

Other ophthalmic formulations and delivery devices are described in U.S. Pat. Nos. 4,014,335; 4,300,557; 5,098,443; 5,188,826; 5,378,475; 5,422,116; 5,424,078; 5,466,233; 5,725,493; 5,773,019; 5,773,021; 5,776,445; 5,814,635; 5,888,493; 6,235,781; 6,297,228; 6,372,245; 6,511,660; 6,579,519; 6,582,422; 6,713,081; 6,719,750; and U.S. Patent Application Publication Nos. 2002-0064513; 2003-0232089; and 2005-0234018.

Kits

In general, kits of the invention contain a corticosteroid and/or an NsIDI. These compounds can be provided in the kit as separate compositions, or combined into a single composition. The kits of the invention can also contain instructions for the administration of both the corticosteroid and NsIDI.

Kits of the invention can also contain instructions for administering an additional pharmacologically acceptable substance (e.g., dipivefrin, anti-VEGF therapies, photodynamic therapy, NSAIDS, antiallergic agents, antihistamines, glaucoma-treating agents, artificial tears, antibiotics, antiviral agents, and antimycotic agents) with a corticosteroid and/or an NsIDI. This kit may contain any combination of the corticosteroid, NsIDI, and additional pharmaceutically acceptable substance (i.e., any one, two, or three of the above compounds).

Dosages

The lowest approved concentrations for ophthalmic formulations of certain corticosteroids are set forth in Table 1.

TABLE 1

| Ophthalmic corticosteroid | Lowest approved concentration for ophthalmic administration | Lowest standard recommended dosage |
|---|---|---|
| Clocortolone Pivalate | 0.1% | N/A |
| Hydrocortisone | 1.0% | 0.5 µg/3 times daily |
| Dexamethasone | 0.1% | 0.05 µg/4-6 times daily |
| Fluorometholone | 0.1% | 0.05 µg/2-4 times daily |
| Loteprednol Etabonate | 0.2% | 0.1 µg/4 times daily |
| Medrysone | 1.0% | 0.5 µg/up to every 4 hours |
| Prednisolone Acetate | 0.12% | 0.06 µg/2-4 times daily |
| Rimexolone | 1.0% | 0.5 µg/4 times daily |

(N/A = Not Available)

In general, a corticosteroid can be administered at a concentration between 0.01% and 5% (e.g., 5.0%, 4.0%, 3.0%, 2.0%, 1.0%, 0.9%, 0.8%, 0.7%, 0.6%, 0.5%, 0.1%, 0.09%, 0.08%, 0.07%, 0.06%, 0.05%, and 0.01%).

Low concentrations of corticosteroids of the invention are 95% or less of the lowest approved concentration. For example, low concentrations of corticosteroids of the invention can be 90%, 85%, 80%, 70%, 60%, 50%, 25%, 10%, 5%, 2%, 1%, 0.5% or 0.1% of the lowest approved concentration.

For example, a low concentration of clocortolone pivalate is between 0.01% and 0.1% (e.g., 0.1%, 0.09%, 0.08%, 0.07%, 0.06%, 0.05%, and 0.01%), a low concentration of hydrocortisone is between 0.01% and 1.0% (e.g., 1.0%, 0.9%, 0.8%, 0.7%, 0.6%, 0.5%, 0.1%, 0.09%, 0.08%, 0.07%, 0.06%, 0.05%, and 0.01%), a low concentration of dexamethasone is between 0.01% and 0.1% (e.g., 0.1%, 0.09%, 0.08%, 0.07%, 0.06%, 0.05%, and 0.01%), a low concentration of fluorometholone is between 0.01% and 0.1% (e.g., 0.1%, 0.09%, 0.08%, 0.07%, 0.06%, 0.05%, and 0.01%), a low concentration of loteprednol etabonate is between 0.01% and 0.2% (e.g., 0.2%, 0.1%, 0.09%, 0.08%, 0.07%, 0.06%, 0.05%, and 0.01%), a low concentration of medrysone is between 0.01% and 1.0% (e.g., 1.0%, 0.9%, 0.8%, 0.7%, 0.6%, 0.5%, 0.1%, 0.09%, 0.08%, 0.07%, 0.06%, 0.05%, and 0.01%), a low concentration of rimexolone is between 0.01% and 1.0% (e.g., 1.0%, 0.9%, 0.8%, 0.7%, 0.6%, 0.5%, 0.1%, 0.09%, 0.08%, 0.07%, 0.06%, 0.05%, and 0.01%), and a low concentration of prednisolone is between 0.01% and 0.12% (e.g., 0.12%, 0.1%, 0.09%, 0.08%, 0.07%, 0.06%, 0.05%, and 0.01%).

The lowest approved ophthalmic concentration of cyclosporine A is 0.05%. Low concentrations of cyclosporine A are 0.04%, or more preferably 0.03%, 0.02%, 0.01%, 0.008%, 0.005%, or 0.001%. The standard daily ophthalmic dosage of cyclosporine A is 0.2 µg twice daily.

Continuous daily dosing with the combinations of the invention may not be required. A therapeutic regimen may require cycles, during which time a drug is not administered, or therapy may be provided on an as needed basis during periods of acute inflammation.

The compound may be administered by methods described herein (e.g., the compound can be administered topically in the form of foams, lotions, drops, creams, ointments, emulsions, or gels).

In order to test the efficacy of the proposed low concentrations and ratios of the corticosteroid and cyclosporine combination for back-of-the-eye diseases, a rabbit model of retinal vein occlusion is utilized. Since corticosteroids may modulate VEGF-mediated responses in vivo, the effects of the low-concentration corticosteroid and cyclosporine combination are evaluated in a rabbit model of VEGF-induced blood-retinal barrier and blood-aqueous (iris) barrier breakdown. VEGF injected intravitreally induces a time and dose-dependent breakdown of the blood-retinal and blood-aqueous barriers. VEGF 165 or vehicle is first injected intravitreally in female Dutch Belt rabbits, and scanning ocular fluorophotometry is used to non-invasively measure the fluorescein leakage from retinal and iris vasculature. Subsequently, the rabbits are treated with either the low-concentration corticosteroid and cyclosporine or vehicle (s.c. or intravitreal) to determine its efficacy on inhibiting the blood-retinal barrier and blood-aqueous breakdown. The effects of corticosteroid and cyclosporine or vehicle on VEGF-induced retinal vasculopathy are further assessed with fundus imaging, fluorescein angiography, and ocular coherence tomography. Additional methods for determining the low concentrations of the invention for the treatment of back-of-the-eye diseases are set forth in Qui et al., Exp Eye Res. 83:141 2006; Manzano et al., Retina. 26:257 2006; Edelman et al., Exp Eye Res. 80:249 2005; Arroyo et al., Jpn J Ophthalmol. 45:359 2001; Ieki et al., Curr Eye Res. 25:317 2002; and Takei et al., Graefes Arch Clin Exp Ophthalmol. 231:476 1993, each of which is hereby incorporated by reference in its entirety.

In order to test the efficacy the proposed low concentrations and ratios of the corticosteroid and cyclosporine combination for front-of-the-eye diseases a murine model of keratoconjunctivitis sicca is used. In one example, dry eye is induced in mice by subcutaneous injection of scopolamine and by exposing them to an air draft and low-humidity environment for 12 days. After 12 days, the mice are killed, and the eyes and eyelids are excised, frozen, and cryosectioned. Transmission electron microscopy (TEM) is performed on conjunctival and corneal samples are taken from the eyes. The effect of low-concentration corticosteroid and cyclosporine on apoptosis is detected in frozen sections with the ApopTag (ISOL) In Situ Oligo Ligation Kit, which specifically detects DNA fragmentation. Immunohistochemical staining is performed to detect activated caspase-3. Conjunctival goblet cell number is counted in tissue sections stained with period acid Schiff (PAS) reagent. These assays are used to determine the effects of low-concentration corticosteroid and cyclosporine on its ability to reduce conjunctival epithelial apoptosis and protect against goblet cell loss. Additional methods for determining the low concentrations for treating front-of-the-eye diseases are set forth in Strong et al. Cornea. 24:80 2005; Luo et al., Invest Ophthalmol Vis Sci. 45:4293 2004; Yeh et al., Invest Ophthalmol Vis Sci. 44:124 2003; and Pflugfelder et al., Am J Pathol. 166:61 2005, each of which is hereby incorporated by reference in its entirety.

Additional Applications

The compounds of the invention can be employed in immunomodulatory or mechanistic assays to determine whether other combinations, or single agents, are as effective as the combination in inhibiting secretion or production of proinflammatory cytokines or modulating immune response using assays generally known in the art, examples of which are described herein. After a suitable time, the cells are examined for cytokine secretion or production or other suitable immune response. The relative effects of the combinations versus each other, and versus the single agents are compared, and effective compounds and combinations are identified.

The combinations of the invention are also useful tools in elucidating mechanistic information about the biological pathways involved in inflammation. Such information can lead to the development of new combinations or single agents for inhibiting inflammation caused by proinflammatory cytokines. Methods known in the art to determine biological pathways can be used to determine the pathway, or network of pathways affected by contacting cells stimulated to produce proinflammatory cytokines with the compounds of the invention. Such methods can include, analyzing cellular constituents that are expressed or repressed after contact with the compounds of the invention as compared to untreated, positive or negative control compounds, and/or new single agents and combinations, or analyzing some other metabolic activity of the cell such as enzyme activity, nutrient uptake, and proliferation. Cellular components analyzed can include gene transcripts, and protein expression. Suitable methods can include standard biochemistry techniques, radiolabeling the compounds of the invention (e.g., $^{14}C$ or $^{3}H$ labeling), and observing the compounds binding to proteins, e.g. using 2d gels, gene expression profiling. Once identified, such compounds can be used in in vivo models to further validate the tool or develop new anti-inflammatory agents.

Experimental Results

Both corticosteroids and NsIDIs suppress cytokine production in cell culture models of immune function. We tested the effect of the combination of various concentrations of NsIDIs and corticosteroids on cytokine production in a cell culture model of immune function. We propose that combinations that demonstrate synergistic or superaddative effects can be used to treat ophthalmic disorders at concentrations low enough to avoid undesired side effects.

Assay for Proinflammatory Cytokine-Suppressing Activity

Compound dilution matrices were assayed for the suppression of IFNγ, IL-2, and TNFα, as described below. The results from these experiments are set forth in FIGS. 1A-1LL.

IFNγ

A 100 µL suspension of diluted human white blood cells contained within each well of a polystyrene 384-well plate (NalgeNunc) was stimulated to secrete IFNγ by treatment with a final concentration of 10 ng/mL phorbol 12-myristate 13-acetate (Sigma, P-1585) and 750 ng/mL ionomycin (Sigma, I-0634). Various concentrations of each test compound were added at the time of stimulation. After 16-18 hours of incubation at 37° C. in a humidified incubator, the plate was centrifuged and the supernatant transferred to a white opaque polystyrene 384 well plate (NalgeNunc, Maxisorb) coated with an anti-IFNγ antibody (Endogen, #M-700A-E). After a two-hour incubation, the plate was washed (Tecan PowerWasher 384) with phosphate buffered saline (PBS) containing 0.1% Tween 20 (polyoxyethylene sorbitan monolaurate) and incubated for an additional one hour with another anti-IFNγ antibody that was biotin labeled (Endogen, M701B) and horseradish peroxidase (HRP) coupled to strepavidin (PharMingen, #13047E). After the plate was washed with 0.1% Tween 20/PBS, an HRP-luminescent substrate was added to each well and light intensity measured using a LJL Analyst plate luminometer.

IL-2

A 100 µL suspension of diluted human white blood cells contained within each well of a polystyrene 384-well plate (NalgeNunc) was stimulated to secrete IL-2 by treatment with a final concentration of 10 ng/mL phorbol 12-myristate 13-acetate (Sigma, P-1585) and 750 ng/mL ionomycin (Sigma, I-0634). Various concentrations of each test compound were added at the time of stimulation. After 16-18 hours of incubation at 37° C. in a humidified incubator, the plate was centrifuged and the supernatant transferred to a white opaque polystyrene 384 well plate (NalgeNunc, Maxisorb) coated with an anti-IL-2 antibody (PharMingen, #555051). After a two-hour incubation, the plate was washed (Tecan PowerWasher 384) with PBS containing 0.1% Tween 20 and incubated for an additional one hour with another anti-IL-2 antibody that was biotin labeled (Endogen, M600B) and HRP coupled to strepavidin (PharMingen, #13047E). After the plate was washed with 0.1% Tween 20/PBS, an HRP-luminescent substrate was added to each well and light intensity measured using a LJL Analyst plate luminometer.

TNFα

The effects of test compound combinations on TNFα secretion were assayed in white blood cells from human buffy coat stimulated with phorbol 12-myistate 13-acetate as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 µL of the diluted white blood cells was placed in each well of the assay plate. Drugs were added to the indicated concentration. After 16-18 hours of incubation at 37° C. with 5% $CO_2$ in a humidified incubator, the plate was centrifuged and the supernatant transferred to a white opaque polystyrene 384-well plate (NalgeNunc, Maxisorb) coated with an anti-TNFα antibody (PharMingen, #551220). After a two-hour incubation, the plate was washed (Tecan Powerwasher 384) with PBS containing 0.1% Tween 20 and incubated for one additional hour with biotin labeled anti-TNFα antibody (PharMingen, #554511) and HRP coupled to streptavidin (PharMingen, #13047E). The plate was then washed again with 0.1% Tween 20/PBS. An HRP-luminescent substrate was added to each well, and the light intensity of each well was measured using a plate luminometer.

Percent Inhibition

The percent inhibition (%I) for each well was calculated using the following formula:

%$I$=[(avg. untreated wells−treated well)/(avg. untreated wells)]×100

The average untreated well value (avg. untreated wells) is the arithmetic mean of 40 wells from the same assay plate treated with vehicle alone. Negative inhibition values result from local variations in treated wells as compared to untreated wells.

Preparation of Compounds

The stock solution containing cyclosporin A was made at a concentration of 1.2 mg/ml in DMSO. The stock solution of tacrolimus was made at a concentration of 0.04 mg/ml in DMSO. Stock solutions containing a corticosteroid were made in dimethylsulfoxide (DMSO) at a final concentration of between 0 and 40 µM. Master plates were prepared to contain dilutions of the stock solutions of the compounds described above. Master plates were sealed and stored at −20° C. until ready for use.

The final single agent plates were generated by transferring 1 µL of stock solution from the specific master plate to a dilution plate containing 100 µL of media (RPMI; Gibco BRL, #11875-085), 10% fetal bovine serum (Gibco BRL, #25140-097), 2% Penicillin/Streptomycin (Gibco BRL, #15140-122)) using the Packard Mini-Trak liquid handler. This dilution plate was then mixed and a 5 mL aliquot transferred to the final assay plate, which had been pre-filled with 50 mL/well RPMI media containing the appropriate stimulant to activate IFNγ, IL-2, or TNFα secretion.

OTHER EMBODIMENTS

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. A composition suitable for ophthalmic administration comprising prednisolone acetate and cyclosporine A wherein said prednisolone acetate is present at a concentration of 0.12% and said cyclosporine A is present at a concentration of 0.01%.

2. A composition suitable for ophthalmic administration comprising prednisolone acetate and cyclosporine A wherein said prednisolone acetate is present at a concentration of 0.12% and said cyclosporine A is present at a concentration of 0.02%.

3. The composition of claim 1, wherein said composition is a solution, gel, ointment, suspension, or emulsion.

4. The composition of claim 1, wherein said prednisolone acetate and said cyclosporine A are the sole active ingredients.

5. The composition of claim 2, wherein said composition is a solution, gel, ointment, suspension, emulsion.

6. The composition of claim 2, wherein said prednisolone acetate and said cyclosporine A are the sole active ingredients.

* * * * *

UNITED STATES PATENT AND TRADEMARK OFFICE
CERTIFICATE OF CORRECTION

| | | |
|---|---|---|
| PATENT NO. | : 8,067,433 B2 | Page 1 of 1 |
| APPLICATION NO. | : 11/594428 | |
| DATED | : November 29, 2011 | |
| INVENTOR(S) | : Chappell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 956 days.

Signed and Sealed this
Third Day of April, 2012

David J. Kappos
*Director of the United States Patent and Trademark Office*